United States Patent
Wu et al.

(10) Patent No.: US 7,273,864 B2
(45) Date of Patent: Sep. 25, 2007

(54) COMPOSITIONS AND METHODS FOR INDUCING OSTEOGENESIS

(75) Inventors: Xu Wu, San Diego, CA (US); Sheng Ding, San Diego, CA (US); Nathanael S. Gray, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/687,220

(22) Filed: Oct. 15, 2003

(65) Prior Publication Data

US 2004/0157864 A1  Aug. 12, 2004

Related U.S. Application Data

(60) Provisional application No. 60/488,699, filed on Jul. 18, 2003, provisional application No. 60/418,898, filed on Oct. 15, 2002.

(51) Int. Cl.
| | | |
|---|---|---|
| C07D 473/40 | (2006.01) | |
| C07D 473/34 | (2006.01) | |
| C07D 473/18 | (2006.01) | |
| A61K 31/522 | (2006.01) | |
| A61K 31/52 | (2006.01) | |

(52) U.S. Cl. ............... 514/234.2; 514/263.37; 514/263.38; 514/263.4; 544/118; 544/276; 544/277

(58) Field of Classification Search ............. 544/118, 544/276, 277; 514/234.2, 263.37, 263.38, 514/263.4
See application file for complete search history.

(56) References Cited

U.S. PATENT DOCUMENTS

| | | | |
|---|---|---|---|
| 5,942,225 A | | 8/1999 | Bruder et al. |
| 6,255,485 B1 * | | 7/2001 | Gray et al. ............ 544/277 |
| 6,369,029 B1 | | 4/2002 | Andress et al. |
| 2002/0016329 A1 * | | 2/2002 | Imbach et al. ......... 544/277 |
| 2005/0043328 A1 * | | 2/2005 | Dolezal et al. ....... 514/263.37 |
| 2005/0124637 A1 * | | 6/2005 | Cheng et al. ......... 514/263.2 |

FOREIGN PATENT DOCUMENTS

| | | |
|---|---|---|
| FR | 2 793 794 A1 | 11/2000 |
| WO | WO 200071543 A1 * | 11/2000 |

OTHER PUBLICATIONS

Montgomery, J.A.C.S. 83, 630 (1961).*
Kelley, J. Med. Chem. 33, 1360 (1990).*
Imbach, Bioorganic & Med. Chem. Letters 9 91-96 (1999).*
Basyouni, Egyptian J. Chem 42(6), 587 (1999).*
Chen, S., et al., "Dedifferentiation of Lineage-Committed Cells by a Small Molecule," *J.Am. Chem. Soc.*, 2004, pp. 410-411, vol. 126, The American Chemical Society.
Imbach, P., et al., "2,6,9-Trisubstituted Purines: Optimization Towards Highly Potent and Selective CDK1 Inhibitors," *Bioorganic & Medicinal Chemistry Letters*, 1999, pp. 91-96, vol. 9, Elsevier Science Ltd.
Keliey, J., et al., "Antirhinovirus Activity of 6-Anilino-9-benzyl-2-chloro-9H-purines," *J. Med. Chem*, 1990, pp. 1360-1363, vol. 33, American Chemical Society.
Montgomery, J., et al., "Synthesis of Potential Anticancer Agents. XXVI. The Alkylation of 6-Chloropurine," Feb. 5, 1961, pp. 630-635, vol. 83.

* cited by examiner

*Primary Examiner*—Mark L. Berch
(74) *Attorney, Agent, or Firm*—Townsend and Townsend and Crew LLP

(57) ABSTRACT

The present invention provides compositions and methods for differentiating and transdifferentiating mammalian cells into cells of an osteoblast lineage, using compounds of the following formula:

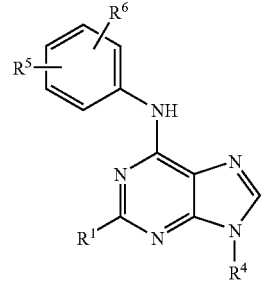

wherein $R^4$ is a functional group including, for example, $C_{1-4}$alkyl, $C_{3-8}$cycloalkyl, hydroxyl-$C_{1-4}$alkyl, aryl-$C_{0-3}$alkyl, substituted with 0-2 $R^{4a}$ groups, and heterocyclo-$C_{0-2}$alkyl, optionally substituted with $C_{1-4}$alkyl; $R^5$ is hydrogen and $R^6$ is a functional group including, for example, halogen, $C_{1-4}$alkyl, —C(O)—$C_{1-4}$alkyl, —SO$^2$—N($R^{2b}$ $R^{2b}$), halo—$C_{1-4}$alkyl, —O-aryl and —N($R^7$ $R^8$), or when $R^5$ and $R^6$ are on adjacent ring atoms they are optionally taken together to form —O—(CH$_2$)$_{1-2}$—O—; and all pharmaceutically acceptable salts and hydrates thereof.

51 Claims, 5 Drawing Sheets

COMPOSITIONS AND METHODS FOR INDUCING OSTEOGENESIS

RELATED APPLICATIONS

This patent application claims the benefit of U.S. Provisional Patent Application No. 60/418,898, filed Oct. 15, 2002, and U.S. Provisional Patent Application No. 60/488,699, filed Jul. 18, 2003, the teachings of both of which are incorporated herein by reference.

BACKGROUND OF THE INVENTION

Bone is a dynamic tissue, with a structure comprising a mineral phase associated with an organic matrix. Homeostasis in the adult skeleton requires a balance between bone resorption and bone formation. During resorption, special cells on the bone's surface dissolve bone tissue and create small cavities. During formation, other cells fill the cavities with new bone tissue. An imbalance in the bone remodeling cycle may cause bone loss that eventually leads to bone-related diseases. Cells of an osteoblast lineage (osteoblasts) play a key role in the balance of the bone remodeling cycle by synthesizing and depositing new bone matrix (osteogenesis). Cells of an osteoblast lineage differentiate from mesenchymal stem cells (i.e., mesenchymal precursor cells). Misregulation of the differentiation of mesenchymal precursor cells into osteoblasts may account for several bone related diseases associated with defective osteoblasts (see, e.g., Olsen et al., *Ann. Rev. Cell Dev. Biol.* 16:191 (2000)), such as, for example, osteoporosis, rickets, osteomalacia, McCune-Albright syndrome, and Paget's disease.

Compositions that stimulating osteogenesis can conveniently be used in therapeutic methods (e.g., oral administration) to treat or prevent these and other disorders. In addition, cells of an osteoblast lineage can conveniently be used in therapeutic methods (e.g., transplantation) to treat or prevent these and other disorders. Methods of stimulating osteogenesis have been described in e.g., U.S. Pat. Nos. 6,369,029 and 5,942,225. It has been difficult, however, to obtain osteoblasts in sufficient numbers to enable effective therapy. For example, U.S. Pat. No. 5,942,225 describes in vitro culture conditions that induce differentiation of human mesenchymal stem cells into cells of an osteogenic lineage using a combination of a steroid (dexamethasone), β-glycerolphosphate and ascorbic acid. However, steroids such as dexamethasone are potent anti-inflammatory drugs that have multiple side-effects. Thus, compositions and methods for appropriate regulation of the proliferation and differentiation of mesenchymal stem cells into cells of an osteoblast lineage has remained elusive.

Thus, there is a need in the art for compositions and methods for inducing differentiation and transdifferentiation of mammalian cells into cells of an osteoblast lineage in vivo and in vitro. There is a particular need for small molecules that can induce in vivo and in vitro differentiation and transdifferentiation of mammalian cells into cells of an osteoblast lineage. The present invention satisfies these and other needs.

SUMMARY OF THE INVENTION

The present invention provides novel compositions and methods for inducing in vivo and in vitro differentiation and transdifferentiation of mammalian cells into cells of an osteoblast lineage.

One embodiment of the present invention provides compounds of Formula I:

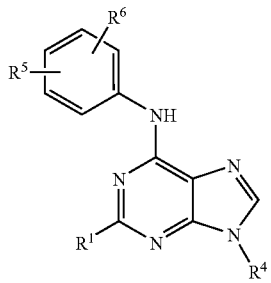

wherein:

$R^1$ is a functional group including, but not limited to, hydrogen, halogen and -L-$R^2$;

L is a functional group including, but not limited to, —O— and —N$R^3$—, wherein $R^3$ is H, or $R^3$ is optionally taken together with $R^2$ and the nitrogen to which both are attached to form a heterocycle, optionally substituted with $C_{1-4}$alkyl;

$R^2$ is a functional group including, but not limited to, $C_{1-4}$alkyl, $C_{3-8}$cycloalkyl and aryl-$C_{0-2}$alkyl, substituted with 0-2 $R^{2a}$ groups that are independently selected and that are functional groups including, but not limited to, halogen, $C_{1-4}$alkyl, $C_{1-4}$alkoxy, —N($R^{2b}$; $R^{2b}$), —SO$_2$N($R^{2b}$; $R^{2b}$), —C(O)N($R^{2b}$; $R^{2b}$) and —O—aryl, or if $R^{2a}$ groups are present and if the two $R^{2a}$ groups are on adjacent ring atoms, they are optionally taken together to form a functional group including, but not limited to, —O—(CH$_2$)$_{1-2}$—O—, —O—C(CH$_3$)$_2$CH$_2$— and —(CH$_2$)$_{3-4}$—;

each $R^{2b}$ group is independently selected and is a functional group including, but not limited to, hydrogen and $C_{1-4}$alkyl;

$R^4$ is a functional group including, but not limited to, $C_{1-4}$alkyl, $C_{3-8}$cycloalkyl, hydroxy-$C_{1-4}$alkyl, aryl-$C_{0-3}$alkyl, substituted with 0-2 $R^{4a}$ groups, cyclohexylmethyl, and heterocyclo-$C_{0-2}$alkyl, optionally substituted with $C_{1-4}$alkyl;

each $R^{4a}$ group is independently selected and is a functional group including, but not limited to, hydrogen, halogen, $C_{1-4}$alkyl, $C_{1-4}$alkoxy, and aryl, or if $R^{4a}$ groups are present and if the two $R^{4a}$ groups are on adjacent ring atoms, they are optionally taken together to form —O—(CH$_2$)$_{1-2}$—O—;

$R^5$ is hydrogen, and $R^6$ is a functional group including, but not limited to, halogen, $C_{1-4}$alkyl, —C(O)-$C_{1-4}$alkyl, —SO$_2$—N($R^{2b}$; $R^{2b}$), $C_{1-4}$alkylhalo, —O-aryl and —N($R^7$; $R^8$), or when $R^5$ and $R^6$ are on adjacent ring atoms they are optionally taken together to form —O—(CH$_2$)$_{1-2}$—O—;

$R^7$ is a functional group including, but not limited to, hydrogen, $C_{1-4}$alkyl, hydroxy-$C_{1-4}$alkyl, aryl and —C(O)$R^{7a}$;

$R^{7a}$ is a is a functional group including, but not limited to, $C_{1-4}$alkyl, $C_{1-4}$alkylhalo, $C_{3-8}$cycloalkyl and aryl; and $R^8$ is a functional group including, but not limited to, H and $C_{1-4}$alkyl, or $R^7$ and $R^8$ are optionally taken together with the nitrogen to which they are attached to form a heterocycloalkyl, optionally substituted with $C_{1-4}$alkyl.

The compounds of the present invention include all pharmaceutically acceptable salts, isomers, solvates, hydrates and prodrugs thereof.

In another embodiment, the present invention provides methods of inducing osteogenesis. Mammalian cells are contacted with a compound of Formula I, whereupon the mammalian cell differentiates into a cell of an osteoblast lineage. The step of contacting can be in vivo or in vitro. In view of their ability to induce osteogenesis, the compounds of Formula I are useful for treating bone disorders and diseases, such as osteoporosis, rickets, osteomalacia, McCune-Albright syndrome, and Paget's disease.

Another embodiment of the present invention provides methods of treating bone disorders by contacting a mammalian cell with a compound of Formula I, whereupon the mammalian cell differentiates into a cell of an osteoblast lineage. The mammalian cell may be further contacted with bone morphogenetic protein 4 (BMP-4). If the mammalian cell is contacted with a compound of Formula I in vitro, the differentiated cells are administered to an individual with the disorder, thereby treating the disorder. In some embodiments, the mammalian cell is attached to a solid support (e.g., a three dimensional matrix or a planar surface).

In some embodiments, the mammalian cell is contacted with a compound of Formula I in vivo. If the mammalian cell is contacted with a compound of Formula I in vivo, the step of contacting may be by oral, intravenous, subcutaneous, or intraperitoneal administration of the compound to the mammal.

In some embodiments, the differentiation of the of the mammalian cell into a cell of an osteoblast lineage is detected. In some embodiments, the differentiation of the of the mammalian cell into a cell of an osteoblast lineage is detected by detecting expression of an osteogenesis marker gene (e.g., alkaline phosphatase, collagen type I, osteocalcin, or osteoponin). In other embodiments, the differentiation of the mammalian cell into a cell of an osteoblast lineage is detected by detecting expression of a bone specific transcription factor (e.g., Cbfa1/Runx2 or Osx).

In some embodiments, the mammalian cell is a stem cell, (e.g., a mesenchymal stem cell, a pre-osteoblast cell, a pre-adipocyte cell, or a myoblast cell). In some embodiments, the mesenchymal stem cell is isolated from a mouse (e.g., a murine embryonic mesoderm fibroblast cell) or from a primate (e.g., a human).

Other embodiments and advantages of the present invention will be apparent from the detailed description that follows.

BRIEF DESCRIPTION OF THE DRAWINGS

FIG. 4A illustrates results demonstrating that Compound A is a potent inducer of osteogenesis in multipotent C3H10T1/2 cells. C3H10T1/2 cells were treated with DMSO alone (control); BMP-4 alone; and Compound A alone (2 µM). Alkaline phosphatase (ALP) activity was measured after two, four, and six days of treatment. FIG. 4B illustrates Cbfa1 gene upregulation in C3H10T1/2 cells in the presence of Compound A.

DETAILED DESCRIPTION OF THE INVENTION AND PREFERRED EMBODIMENTS

I. Introduction

Figure 1:
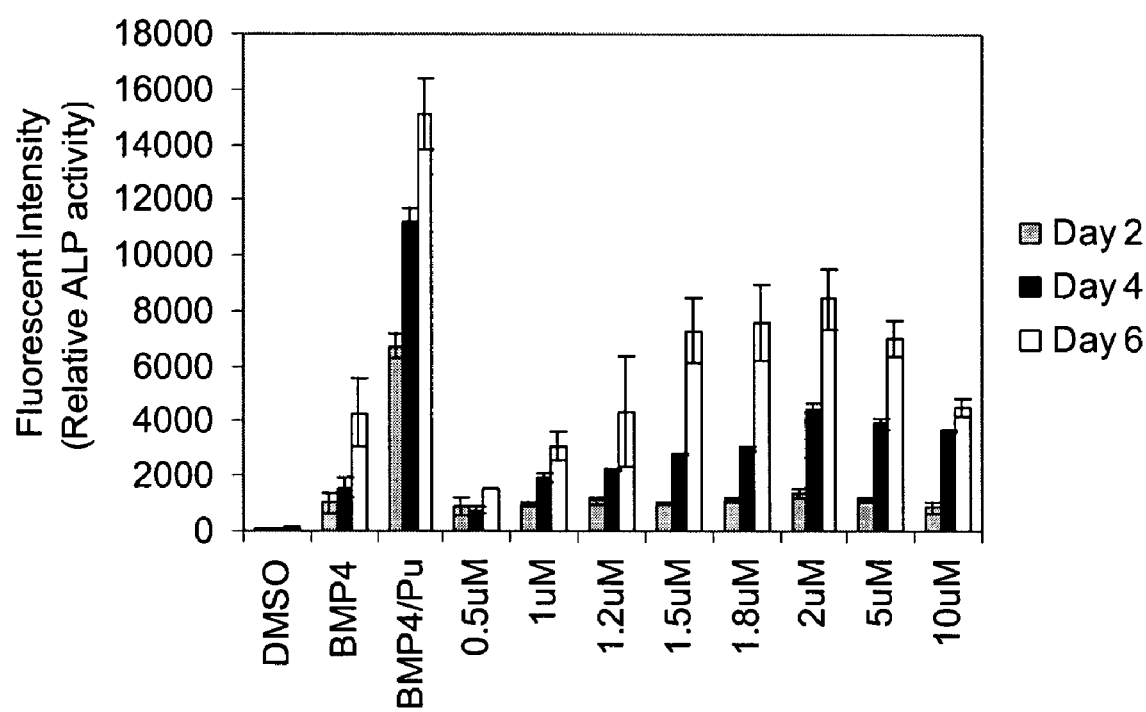
FIG. 1 illustrates results demonstrating that Compound A is a potent inducer of osteogenesis in multipotent C3H10T1/2 cells. C3H10T1/2 cells were treated with DMSO alone (control); BMP-4 alone (300 ng/mL); BMP-4 (100 ng/mL) and Compound A (1 µM); or 0.5 µM, 1 µM, 1.2 µM, 1.5 µM, 1.8 µM, 2 µM, 5 µM, or 10 µM Compound A alone. Alkaline phosphatase (ALP) activity was measured after two, four, and six days of treatment.

The present invention provides compounds, compositions and methods for differentiating and transdifferentiating mammalian cells into cells of an osteoblast lineage. More particularly, the present invention provides compounds of Formula I that are useful for differentiating and transdifferentiating mammalian cells into cells of an osteoblast lineage. In some embodiments, a composition comprising the compound of Formula I is provided. In other embodiments, methods of inducing osteogenesis in mammalian cells are provided. Osteogenesis can be induced in vivo or in vitro according to the methods of the present invention.

II. Definitions

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

The term "alkyl," by itself or as part of another substituent, means, unless otherwise stated, a straight or branched chain saturated hydrocarbon radical, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—O—$CH_2$—$CH_2$—$(CH_3)_2$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si$(CH_3)_3$, —$CH_2$—CH=N—$OCH_3$, and —CH=CH—N$(CH_3)$—$CH_3$. Up to two heteroatoms may be consecutive, such as, for example, —$CH_2$—NH—$OCH_3$ and —$CH_2$—O—Si$(CH_3)_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, an aromatic, hydrocarbon substituent, which can be a single ring or multiple rings (up to three rings), which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by an oxygen atom (e.g., phenoxymethyl, 2-pyridyloxymethyl, 3-(1-naphthyloxy)propyl, and the like), with the proviso that the carbon atom is not a radical.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R" R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR"R", —CN and —$NO_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', ,—NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B-, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

As used herein, the term "heteroatom" is meant to include oxygen (O), nitrogen (N) and sulfur (S).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Osteogenesis," as used herein, refers to proliferation of bone cells and growth of bone tissue (i.e., synthesis and deposit of new bone matrix). Osteogenesis also refers to differentiation or transdifferentiation of progenitor or precursor cells into bone cells (i.e., osteoblasts). Progenitor or precursor cells can be pluripotent stem cells such as, e.g., mesenchymal stem cells. Progenitor or precursor cells can be cells pre-committed to an osteoblast lineage (e.g., pre-osteoblast cells) or cells that are not pre-committed to an osteoblast lineage (e.g., pre-adipocytes or myoblasts).

A "stem cell," as used herein, refers to any self-renewing pluripotent cell or multipotent cell or progenitor cell or precursor cell that is capable of differentiating into multiple cell types. Stem cells suitable for use in the methods of the present invention include those that are capable of differentiating into cells of osteoblast lineage, e.g., osteoblasts. Suitable stem cells for use in the methods of the present invention include, for example, mesenchymal stem cells, pre-osteoblast cells, pre-adipocyte cells, and myoblast cells. Mesenchymal stem cells (MSC) are capable of differentiating into the mesenchymal cell lineages, such as bone, cartilage, adipose, muscle, stroma, including hematopoietic supportive stroma, and tendon, and play important roles in repair and regeneration (see, e.g., Olsen, 2000, supra). MSCs are identified by specific cell surface markers which are identified with unique monoclonal antibodies as described in e.g., U.S. Pat. No. 5,643,736.

"Differentiate" or "differentiation," as used herein, refers to the process by which precursor or progenitor cells (i.e., stem cells) differentiate into specific cell types, e.g., osteoblasts. Differentiated cells can be identified by their patterns of gene expression and cell surface protein expression.

Typically, cells of an osteoblast lineage express genes such as, for example, alkaline phosphatase, collagen type I, osteocalcin, and osteoponin. Typically, cells of an osteoblast lineage express bone specific transcription factors such as, for example, Cbfa1/Runx2 and Osx (see, e.g., Olsen et al, 2000 supra and Nakashima et al., *Cell* 108(1):17-29 (2002). Additional transcription factors that are involved in osteoblast differentiation include, e.g., gsc, Dlx1, Dlx5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra).

"Transdifferentiation" refers to the process refers to the process by which precursor or progenitor cells (i.e., stem cells) pre-committed to cell types of one lineage differentiate into specific cell types of another lineage, e.g., pre-adipocytes transdifferentiate into osteoblasts or myoblasts transdifferentiate into osteoblasts. Transdifferentiated cells can be identified by their patterns of gene expression and cell surface protein expression. Typically, cells of an osteoblast lineage express genes such as, for example, alkaline phosphatase, collagen type I, osteocalcin, and osteoponin. Typically, cells of an osteoblast lineage express bone specific transcription factors such as, for example, Cbfa1/Runx2 and Osx (see, e.g., Olsen et al, 2000 supra and Nakashima et al., *Cell* 108(1):17-29 (2002). Additional transcription factors that are involved in osteoblast differentiation include, e.g., gsc, Dlx1, Dlx5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra).

A "solid support," as used herein in connection with inducing osteogenesis, refers to a three-dimensional matrix or a planar surface on which the stem cells can be cultured. The solid support can be derived from naturally occurring substances (i.e., protein based) or synthetic substances. For example, matrices based on naturally occurring substances may be composed of autologous bone fragments or commercially available bone substitutes as described in e.g., Clokie et al., *J. Craniofac. Surg.* 13(1):111-21 (2002) and Isaksson, *Swed. Dent. J. Suppl.* 84:1-46 (1992). Suitable synthetic matrices are described in, e.g., U.S. Pat. Nos. 5,041,138, 5,512,474, and 6,425,222. For example, biodegradable artificial polymers, such as polyglycolic acid, polyorthoester, or polyanhydride can be used for the solid support. Calcium carbonate, aragonite, and porous ceramics (e.g., dense hydroxyapatite ceramic) are also suitable for use in the solid support. Polymers such as polypropylene, polyethylene glycol, and polystyrene can also be used in the solid support. Cells cultured and differentiated on a solid support that is a three-dimensional matrix typically grow on all of the surfaces of the matrix, e.g., internal and external. Cells cultured and differentiated on a solid support that is planar typically grow in a monolayer. The term "solid-support" is also used in the context of preparing the compounds of Formula I. In this context, "solid-support" refers to a polymeric support, such as a bead, that can be partially soluble in a suitable solvent or completely insoluble, and is used to bind, for example, a reactant or a reagent of the reaction. Suitable solid-supports include, but are not limited to, PAL resin, Wang resin, and polystyrene resin.

"Culturing," as used herein, refers to maintaining cells under conditions in which they can proliferate, differentiate, and avoid senescence. For example, in the present invention, cultured mesenchymal stem cells proliferate and differentiate into cells of an osteoblastic cell lineage. Cells can be cultured in growth media containing appropriate growth factors, i.e., a growth factor cocktail that contains, for example, bone morphogenetic protein-2 (BMP-2), bone morphogenetic protein-4 (BMP-4), bone morphogenetic protein-7 (BMP-7), or another suitable member of the BMP family of proteins.

III. Compounds of the Present Invention and Methods for their Preparation

A. The Compounds of Formula I

In one aspect, the present invention provides compounds of Formula I:

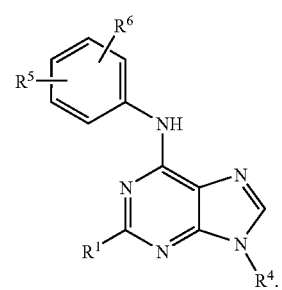

In Formula I, $R^1$ is a functional group including, but not limited to, hydrogen, halogen and —L—$R^2$. L, in connection with $R^1$, is a functional group including, but not limited to, —O— and —$NR^3$—, wherein $R^3$ is H, or $R^3$ is optionally taken together with $R^2$ and the nitrogen to which both are attached to form a heterocycle, optionally substituted with $C_{1-4}$alkyl. $R^2$ is a functional group including, but not limited to, $C_{1-4}$alkyl, $C_{3-8}$cycloalkyl and $C_{0-2}$alkylaryl, substituted with 0-2 $R^{2a}$ groups that are independently selected and that are functional groups including, but not limited to, halogen, $C_{1-4}$alkyl, $C_{1-4}$alkoxy, —N($R^{2b}$, $R^{2b}$), —$SO_2$N($R^{2b}$, $R^{2b}$), —C(O)N($R^{2b}$, $R^{2b}$) and —O-aryl, or if $R^{2a}$ groups are present and if the two $R^{2a}$ groups are on adjacent ring atoms, they are optionally taken together to form a functional group including, but not limited to, —O—$(CH_2)_{1-2}$—O—, —O—$C(CH_3)_2CH_2$— and —$(CH_2)_{3-4}$—. Each $R^{2b}$ group is independently selected and is a functional group including, but not limited to, hydrogen and $C_{1-4}$alkyl In Formula I, $R^4$ is a functional group including, but not limited to, $C_{1-4}$alkyl, $C_{3-8}$cycloalkyl, hydroxy-$C_{1-4}$alkyl, aryl-$C_{0-3}$alkyl, substituted with 0-2 $R^{4a}$ groups, cyclohexylmethyl, and heterocyclo-$C_{0-2}$alkyl, optionally substituted with $C_{1-4}$alkyl. Each $R^{4a}$ group is independently selected and is a functional group including, but not limited to, hydrogen, halogen, $C_{1-4}$alkyl, $C_{1-4}$alkoxy and aryl, or if $R^{4a}$ groups are present and if the two $R^{4a}$ groups are on adjacent ring atoms, they are optionally taken together to form —O—$(CH_2)_{1-2}$—O—;

In Formula I, $R^5$ is hydrogen, and $R^6$ is a functional group including, but not limited to, halogen, $C_{1-4}$alkyl, —C(O)—$C_{1-4}$alkyl, —$SO_2$—N($R^{2b}$, $R^{2b}$), $C_{1-4}$alkylhalo, —O-aryl and —N($R^7$, $R^8$), or when $R^5$ and $R^6$ are on adjacent ring atoms they are optionally taken together to form —O—$(CH_2)_{1-2}$—O—. $R^7$ is a functional group including, but not limited to, hydrogen, $C_{1-4}$alkyl, $C_{1-4}$alkylhydroxy, aryl and —C(O)$R^{7a}$, wherein $R^{7a}$ is a is a functional group including, but not limited to, $C_{1-4}$alkyl, $C_{1-4}$alkylhalo, $C_{3-8}$cycloalkyl and aryl, and $R^8$ is a functional group including, but not limited to, H and $C_{1-4}$alkyl, or $R^7$ and $R^8$ are optionally taken together with the nitrogen to which they are attached to form a heterocycle, optionally substituted with $C_{1-4}$alkyl.

The compounds of the present invention include all pharmaceutically acceptable salts, isomers, solvates, hydrates and prodrugs thereof.

In a preferred embodiment, $R^1$ is a member of the following group of substituents:

In a more preferred embodiment, $R^1$ is a member of the following group of substituents:

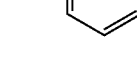

In a most preferred embodiment, $R^1$ is the following:

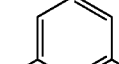

In another preferred embodiment, $R^4$ is a member of the following group:

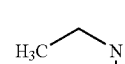

-continued

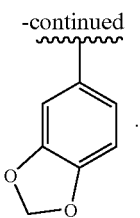

In a more preferred embodiment, $R^4$ is a member of the following group:

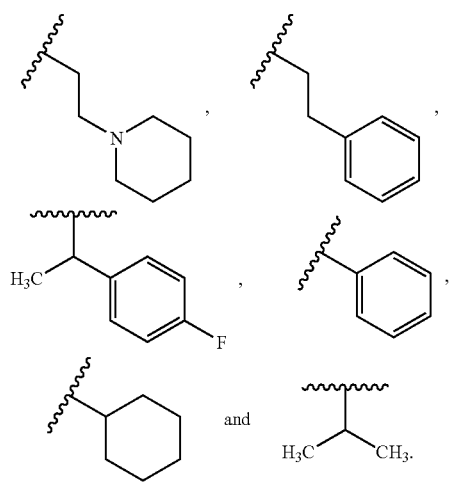

In a most preferred embodiment, $R^4$ is a cyclohexyl group.

In another preferred embodiment, $R^5$ is H and $R^6$ is a member of the group consisting of chloro, —$CF_3$, —$CH_3$, —$C(O)CH_3$, —$SO_2NH_2$, —$NMe_2$, —NHMe, —NHC(O)Me, —$NHC(O)CF_3$, In a further preferred embodiment, $R^5$ and $R^6$ are taken together along with the aniline to which they are attached to form

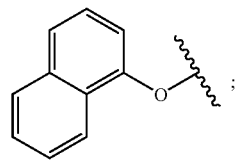

In a most preferred embodiment, $R^5$ is hydrogen and $R^6$ is morpholino.

In a preferred embodiment,
$R^1$ is

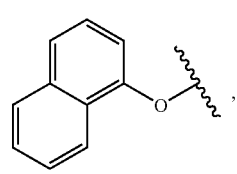

$R^5$ is H; and
$R^6$ is morpholine.

In another preferred embodiment,
$R^1$ is $R^5$ is H;
$R^6$ is morpholine; and
$R^4$ is a member selected from the group consisting of:

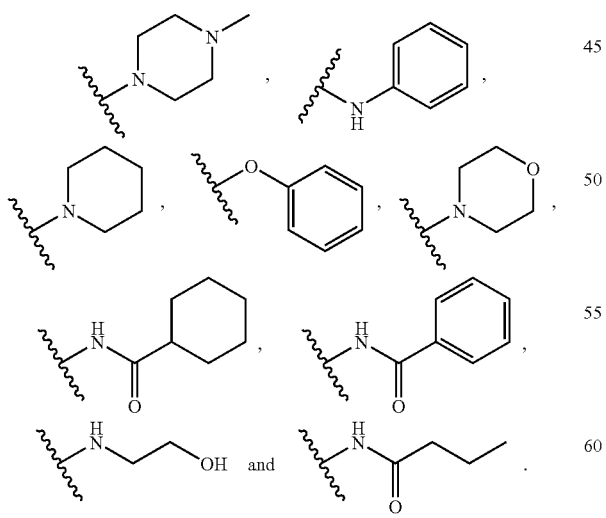

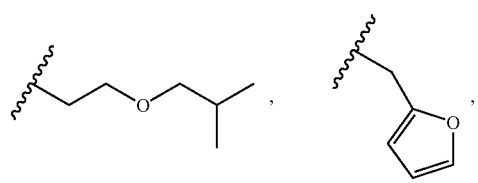
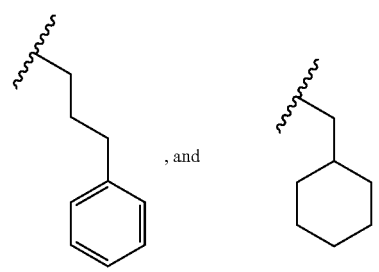, and
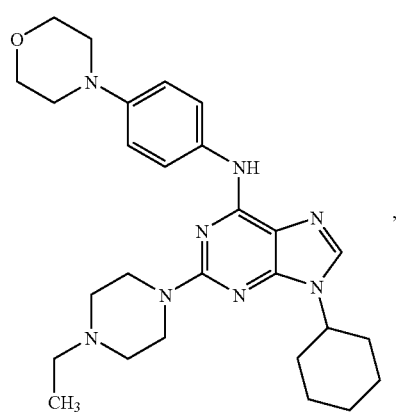.
Preferred compounds of the present invention, include, but are not limited to:
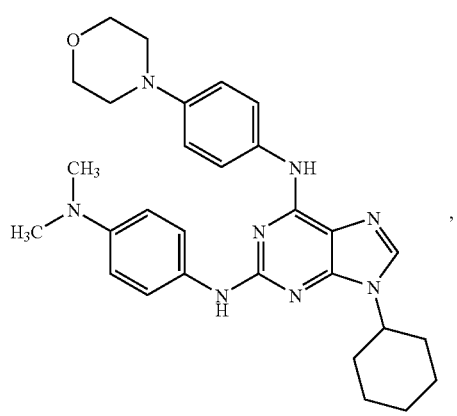
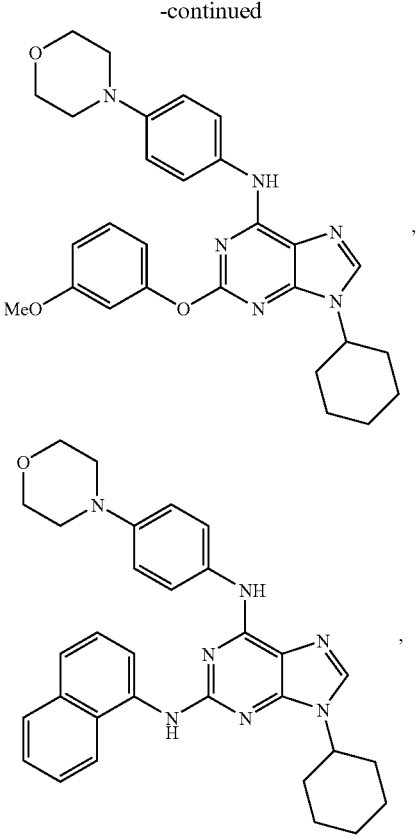
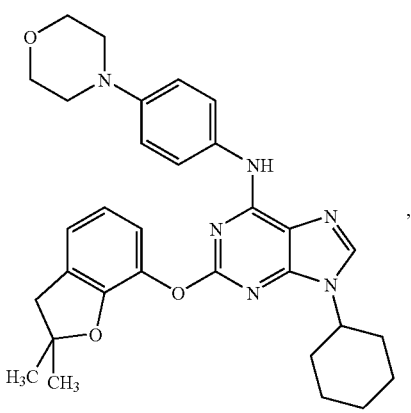
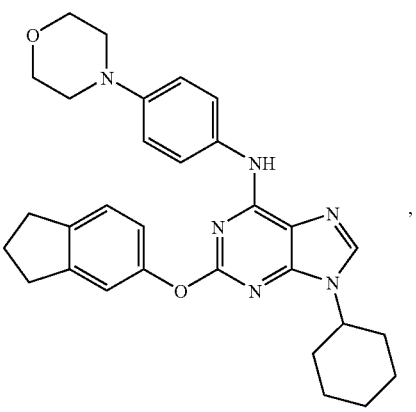

-continued
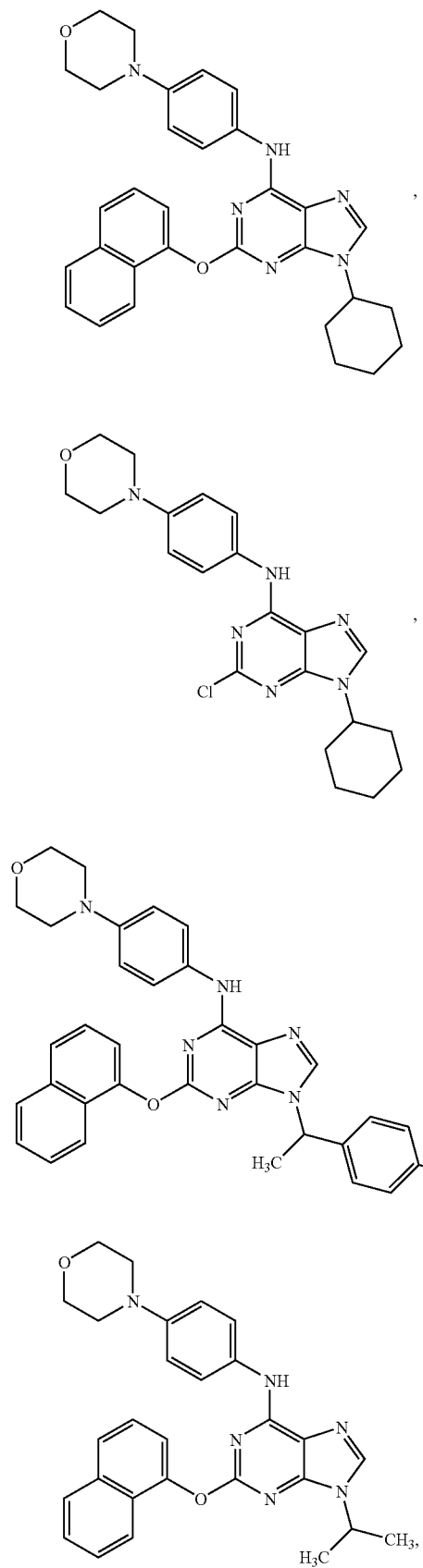
-continued
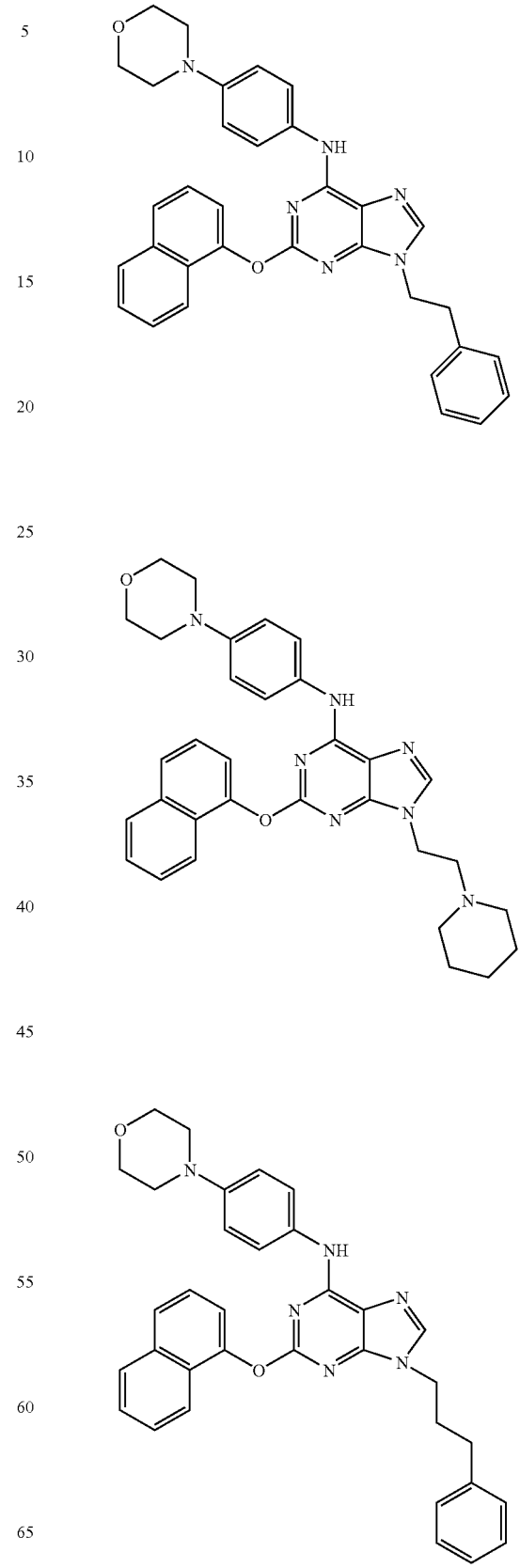

-continued

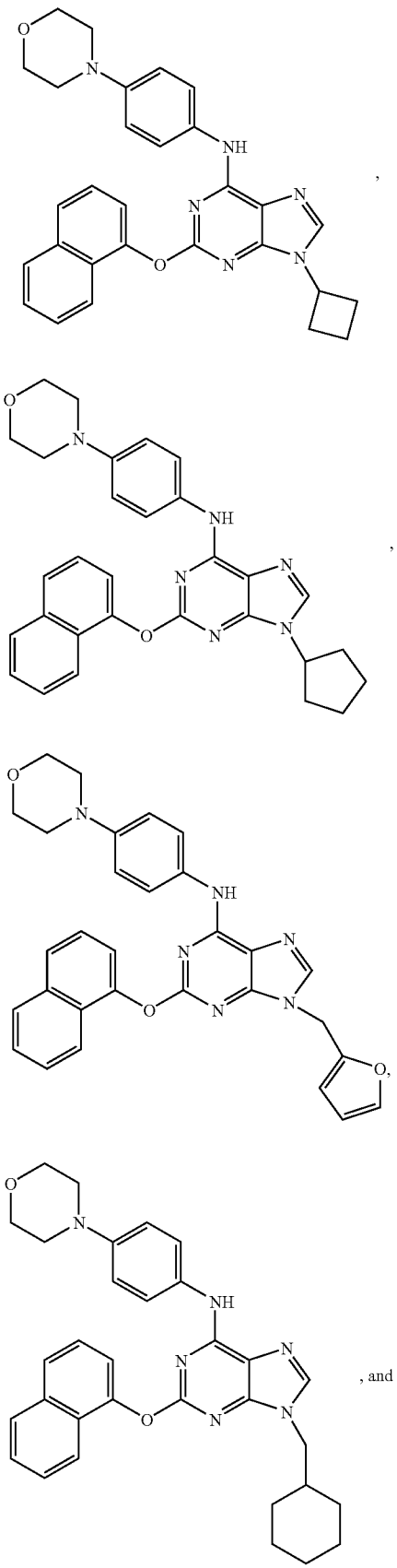

, and

-continued

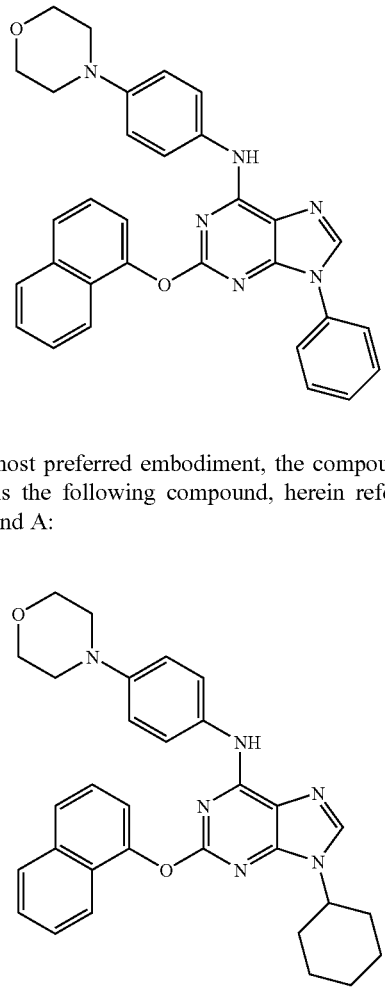

In a most preferred embodiment, the compound of Formula I is the following compound, herein referred to as Compound A:

The compounds of Formula I can be readily screened for their ability to induce osteogenesis using the in vitro and in vitro screening methods set forth below and, in particular, in the examples.

B. Preparation of Compounds

The compounds of the present invention can be prepared by either solid-phase or solution-phase synthesis.

1. Solid-Phase Synthesis

Methods directed to the solid-phase synthesis of the compounds of Formula I are discussed herein in Example I, as well as in U.S. Patent Application No. 60/328,763, filed Oct. 12, 2001, U.S. Patent Application No. 60/331,835, filed Nov. 20, 2001, U.S. Patent Application No. 60/346,480, filed Jan. 7, 2002, U.S. Patent Application No. 60/348,089, filed Jan. 10, 2002, and U.S. Patent Application No. 10/270,030, filed Oct. 12, 2002.

In one aspect, the present invention provides a method for synthesizing a substituted heteroaryl, the method comprising: (a) providing a dihaloheteroaryl scaffold moiety; and (b) capturing the dihaloheteroaryl scaffold moiety on a resin by nucleophilic substitution of a first halogen by a resin-bound amine nucleophile to afford a substituted heteroaryl, e.g., a resin-bound amine substituted monohaloheteroaryl; (c) reacting the second halogen with a suitably substituted amine or aryl alcohol to afford the resin bound substituted heteroaryl; and (d) cleavage of the substituted heteroaryl from the resin.

Suitable resins useful for the present invention include, but are not limited to, PAL resin, Wang resin, and polystyrene resin. Other suitable resins would be clear to a person of skill in the art. In a preferred embodiment, the PAL resin is utilized.

In a preferred embodiment, the two halogens, i.e., halo groups, of the dihaloheteroaryl scaffold moiety are independently selected and include, but are not limited to, chloro, fluoro, bromo and iodo. In a presently preferred embodiments, the two halogens are chloro groups.

In a preferred embodiment, the method further comprises substitution of the second halogen of the dihaloheteroaryl scaffold moiety by nucleophilic displacement or, alternatively, by a coupling reaction. In a presently preferred embodiment, a coupling reaction is employed to carry out the substitution of the second halogen of the dihaloheteroaryl scaffold moiety. In this connection, the coupling reaction is preferably a palladium-mediated coupling reaction.

It will be readily apparent to those of skill in the art that the two halogens, i.e., halo groups, of the dihaloheteroaryl scaffold moiety can be substituted with a number of different functional groups. Suitable functional groups include, but are not limited to, anilines, phenols, amines and boronic acids (see, Table 1). In a preferred embodiment, the functional group includes, but is not limited to, aryl boronic acids, anilines and phenols.

In a preferred embodiment, the method further comprises performing an initial substitution prior to substitution of the first halogen of the dihaloheteroaryl scaffold moiety. In a preferred embodiment, the initial substitution is carried out using a reaction including, but not limited to, alkylation reactions, acylation reactions and coupling reactions.

Numerous dihaloheteroaryl scaffold moieties can be used in the methods of the present invention. Examples of suitable dihaloheteroaryl scaffold moieties include, but are not limited to, purines, pyrimidines, quinazolines, pyrazines, phthalazines, pyradazines and quinoxalines.

When a palladium-catalyzed coupling reaction is employed to substitute the halo groups of the dihaloheteroaryl or the halo group of the resin-bound amine substituted monohaloheteroaryl, the palladium-catalyzed coupling reaction typically involves reacting the dihaloheteroaryl or the resin-bound amine substituted monohaloheteroaryl with a coupling agent in the presence of a solvent, a palladium catalyst, a base and a carbene or phosphine ligand. Suitable coupling agents include, but are not limited to, boronic acids, amines and alcohols. In a presently preferred embodiment, suitable coupling agents include, but are not limited to, aryl boronic acids, anilines and phenols.

In the above methods, carbene or phosphine ligands can be used. Examples of ligands suitable for use in the methods of the present invention include, but are not limited to, the following carbene and phosphine ligands:

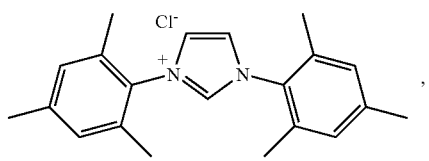

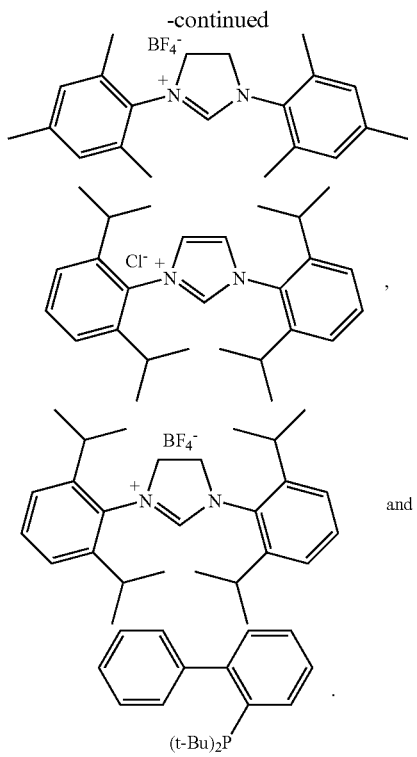
and

In a presently preferred embodiment, the ligand is a phosphine ligand including, but not limited to, the following:

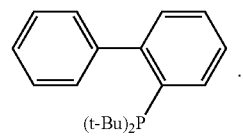

A number of bases can be used in carrying out the methods of the present invention. Examples of bases suitable for use in the above method include, but are not limited to, cesium carbonate, potassium carbonate, sodium carbonate, sodium bicarbonate, potassium bicarbonate, cesium bicarbonate, potassium fluoride, potassium phosphate, potassium tert-butyloxide, sodium tert-butyloxide, and triethylamine.

A number of solvents can be used in carrying out the methods of the present invention. Examples of solvents suitable for use in the above method include, but are not limited to, 1,4-dioxane, tetrahydrofuran, dimethoxyethane (DME), dimethylformamide (DMF), benzene and toluene.

A number of palladium catalysts can be used in carrying out the methods of the present invention. Typically, the oxidation state of the palladium in the catalyst is (O) or (II). Examples of palladium catalysts suitable for use in carrying out the methods of the present invention include, but are not limited to, $Pd_2(dba)_3$, $Pd(OAc)_2$, $Pd(PPh_3)_4$, $Pd(O)$, $PdCl_2$ (dppf) and $PdCl_2$. Such catalysts are known to and used by those of skill in the art and, thus, their structures are known. In a preferred embodiment, the palladium catalyst is $Pd_2(dba)_3$.

In a preferred embodiment, the foregoing methods further comprise cleaving the compound from the solid support. It will be readily appreciated that the compounds of the present invention can be readily cleaved from the solid support using standard methods known to and used by those of skill in the art. Cleavage of a resin-bound compound and liberation of the desired compound from the resin is typically carried in the presence of an acid. Suitable acids include, but are not limited to, an organic acid such as formic acid, acetic acid, propionic acid, trichloroacetic acid, trifluoroacetic acid and the like, and inorganic acids such as hydrochloric acid, hydrobromic acid, sulfuric acid, hydrogen chloride, etc., or the like. The reaction is usually carried out in a solvent such as water, an alcohol such as methanol, ethanol, 1,4, dioxane, methylene chloride, tetrahydrofuran, a mixture thereof or any other solvent which does not adversely influence the reaction.

In yet another aspect of the present invention, the foregoing method is adapted to prepare a library (or an array) of heteroaryl scaffold moieties. Typically, the library of substituted scaffold moieties is prepared using a plurality of dihaloheteroaryl scaffold moieties. As such, in another aspect, the present invention provides a method for synthesizing a combinatorial library of substituted heteroaryls (e.g., heterocycles), the method comprising: providing a plurality of dihaloheterocyclic scaffold moieties; and capturing the dichloroheterocyclic scaffold moieties on a resin by nucleophilic substitution of a first chlorine by a resin-bound amine nucleophile).

In a preferred embodiment, the two halogens, i.e., halo groups, present in the dihaloheteroaryl scaffold moieties are independently selected and include, but are not limited to, chloro, fluoro, bromo and iodo. In a presently preferred embodiments, the two halogens of the dihaloheteroaryl scaffold moieties are chloro groups.

In a preferred embodiment, the method further comprises substitution of the second halogen of the dihaloheteroaryl scaffold moieties by nucleophilic displacement or, alternatively, by a coupling reaction. In a presently preferred embodiment, a coupling reaction is employed to carry out the substitution of the second halogen of the dihaloheteroaryl scaffold moieties. In this connection, the coupling reaction is preferably a palladium-mediated coupling reaction.

It will be readily apparent to those of skill in the art that the two halogens, i.e., halo groups, of the dihaloheteroaryl scaffold moieties can be substituted with a number of different functional groups, each of which is independently selected. Suitable functional groups include, but are not limited to, anilines, phenols, amines and boronic acids (see, Table I). In a presently preferred embodiment, the functional groups include, but are not limited to, aryl boronic acids, anilines and phenols.

In a preferred embodiment, the method further comprises performing initial substitutions prior to substitution of the first halogens of the dihaloheteroaryl scaffold moieties. In a preferred embodiment, the initial substitution is carried out using a reaction including, but not limited to, alkylation reactions, acylation reactions and coupling reactions.

Numerous dihaloheteroaryl scaffold moieties can be used in the methods of the present invention. Examples of suitable dihaloheteroaryl scaffold moieties include, but not limited to, purines, pyrimidines, quinazolines, pyrazines, phthalazines, pyradazines and quinoxalines.

When a palladium-catalyzed coupling reaction is employed to substitute the halo groups of the dihaloheteroaryl scaffold moieties or the halo group of the resin-bound amine substituted monohaloheteroaryls, the palladium-catalyzed coupling reaction typically involves reacting the dihaloheteroaryl or the resin-bound amine substituted monohaloheteroaryl with a coupling agent in the presence of a solvent, a palladium catalyst, a base and a carbene or phosphine ligand. Suitable coupling agents include, but are not limited to, boronic acids, amines and alcohols. In a presently preferred embodiment, suitable coupling agents include, but are not limited to, aryl boronic acids, anilines and phenols. It is noted that the foregoing discussions relating to the carbene or phosphine ligands, bases, solvents, palladium catalysts and copper catalysts set forth in connection with the methods for preparing a C-2 substituted purine compound or a 9-aryl substituted purine compound are fully applicable to the methods for preparing a combinatorial library or array of substituted heteroaryl compound and, thus, they will not be repeated here.

2. Solution-Phase Synthesis

The solution-phase synthesis of the compounds of Formula I involves first substituting 2,6-dihaloheteroaryl with a suitable substituent under appropriate reaction conditions known to one of skill in the art. This is followed by substitution with a suitably substituted aniline under appropriate reaction conditions known to one of skill in the art. Finally, the heteroaryl is substituted by reaction with a suitably substituted amine or arylalcohol using a Pd catalyst under appropriate reaction conditions known to one of skill in the art. It is noted that the foregoing discussions relating to the carbene or phosphine ligands, bases, solvents and palladium catalysts are set forth with the methods for the preparing the compounds of Formula I via solid-support are fully applicable to the methods for preparing the compounds of Formula I via solution phase, and, thus, they will not be repeated here.

IV. Use of the Compounds/Compositions to Induce Osteogenesis

The compositions of the present invention can be used to induce osteogenesis in mammalian cells. A mammalian cell is contacted with a compound of Formula I, whereupon the mammalian cell differentiates into a cell of an osteoblast lineage. The mammalian cell can be contacted with a compound of Formula I (or a composition thereof) either in vivo or in vitro.

A. In Vivo Induction of Osteogenesis

The compounds of Formula I as well as compositions thereof can conveniently be used to induce osteogenesis in vivo. The compounds and compositions of the present invention are administered to an individual, e.g., a mammal such as a human, in an amount effective to induce differentiation of mammalian cells into cells of an osteoblast lineage. In view of their ability to induce osteogenesis, the compounds of Formula I are useful for treating bone disorders and diseases, such as osteoporosis, rickets, osteomalacia, McCune-Albright syndrome, and Paget's disease. In a preferred embodiment, the compounds and compositions of the present invention are used to treat osteoporosis. In a preferred embodiment, the compounds and compositions of the present invention are used to increase bone density. In a particularly preferred embodiment, the compounds and compositions of the present invention are used to increase bone density and reduce bone loss.

One of skill in the art will appreciate that the compositions of the present invention can be used alone or in combination with other compounds and therapeutic regimens to induce osteogenesis. For example, a compound of Formula I may be administered in conjunction with bone morphogenetic proteins or anti-resorptive medications that affect the bone remodeling cycle. Suitable bone morphogenetic proteins include, for example, BMP-2, BMP-4, and BMP-7. Suitable anti-resorptive medications include, for example, bisphosphonates such as, for example, alendronate sodium and risedronate sodium; hormones, such as, for example, calcitonin and estrogens, and selective estrogen receptor modulators, such as, for example, raloxifene.

An effective amount of the composition will be determined by the existence, nature, and extent of any adverse side-effects that accompany the administration of the composition; the LD50 of the composition; and the side-effects of the composition at various concentrations. Typically, the amount of the composition administered will range from about 0.01 to about 20 mg per kg, more typically about 0.05 to about 15 mg per kg, even more typically about 0.1 to about 10 mg per kg body weight.

The compositions can be administered, for example, by intravenous infusion, orally, intraperitoneally, or subcutaneously. Oral administration is the preferred method of administration. The formulations of compounds can be presented in unit-dose or multi-dose sealed containers, such as ampoules and vials.

The compositions of the present invention are typically formulated with a pharmaceutically acceptable carrier before administration to an individual or subject. Pharmaceutically acceptable carriers are determined, in part, by the particular composition being administered (e.g., Compound A), as well as by the particular method used to administer the composition. Accordingly, there are a wide variety of suitable formulations of pharmaceutical compositions of the present invention (see, e.g., Remington's Pharmaceutical Sciences, 17th ed., 1989).

Formulations suitable for oral administration can consist of (a) liquid solutions, such as an effective amount of the compound of Formula I suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of the following: lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compositions of the present invention may be in formulations suitable for other routes of administration, such as, for example, intravenous infusion, intraperitoneally, or subcutaneously. The formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

The dose administered to a patient, in the context of the present invention should be sufficient to effect a beneficial therapeutic response in the patient over time. For example, if the compositions of the present invention are administered to treat or prevent osteoporosis, the dose administered to the patient should be sufficient to prevent, retard, or reverse decreases in bone density. The dose will be determined by the efficacy of the particular composition employed and the condition of the patient, as well as the body weight or surface area of the patient to be treated. The size of the dose also will be determined by the existence, nature, and extent of any adverse side-effects that accompany the administration of a particular composition in a particular patient.

B. In vitro Induction of Osteogenesis

The compositions of the present invention can conveniently be used to induce osteogenesis in vitro. Mammalian cells are contacted with the compositions, whereupon the mammalian cells differentiates into cells of an osteoblast lineage.

1. Suitable Cells

The mammalian cells can be stem cells, typically mesenchymal stem cells (MSCs), pre-osteoblasts, or cells of other lineages such as, for example, pre-adipocytes or myoblasts. Methods for isolation and differentiation of human and animal MSCs have been described (see, e.g., U.S. Pat. Nos. 5,942,225 and 5,486,359; and Pittenger et al., Science 284: 143 (1999)).

Human mesenchymal stem cells (MSC) may be obtained by isolating pluripotent mesenchymal stem cells from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, blood, adipose tissue, and muscle satellite cells. Typically, cells from a tissue specimen containing mesenchymal stem cells are cultured in growth medium containing growth factors that (1) stimulate mesenchymal stem cell growth without differentiation, and (2) allow for the selective adherence of only the mesenchymal stem cells to a substrate surface. After culturing the cells for a suitable amount of time, non-adherent matter is removed from the substrate surface, thus providing an expanded population of mesenchymal stem cells. Thus, homogeneous MSC populations are obtained by positive selection of adherent marrow or periosteal cells which are free of markers associated with either hematopoietic cell or differentiated mesenchymal cells.

The cells to be differentiated into cells of an osteoblast lineage can be derived from any suitable mammal. For example, the cells may be obtained from a rodents such as, for example, mice, rats, guinea pigs, and rabbits; non-rodent mammals such as, for example, dogs, cats, pigs, sheep, horses, cows, and goats; primates such as, for example, chimpanzees and humans. The cells to be differentiated may be primary cells or may be cells maintained in culture. If the cells are maintained in culture, they are typically contacted with the compounds/compositions of the present invention between the 12th and 15th passage in culture. Techniques and methods for establishing a primary culture of cells for use in the methods of the invention are known to those of skill in the art (see, e.g., Humason, ANIMAL TISSUE TECHNIQUES, $4^{th}$ ed., W. H. Freeman and Company (1979), and Ricciardelli et al., (1989) In Vitro Cell Dev. Biol. 25: 1016.

2. General Culturing Methods

The mammalian cells may be contacted with Compound A alone or with Compound A in the presence of other growth factors. Typically, the additional growth factors are BMP-2, BMP-4, BMP-7, or other members of the BMP family of proteins. Those of skill in the art will appreciate that the amount of Compound A and growth factors can be adjusted to facilitate induction of differentiation in particular cell types. Typically, the amount of Compound A contacted with the cells is from about 0.1 µM (52 ng/ml) to about 50 µM (2.6 µg/ml), more typically from about 0.25 µM to about 35 µM, even more typically from about 0.5 µM to about 25 µM, yet more typically from about 0.75 µM to about 15 µM, most typically at about 1 µM. Typically the amount of BMP protein contacted with the cells is from about 1 ng/ml to about 400 ng/ml, more typically from about 25 ng/ml to about 300 ng/ml, even more typically from about 50 ng/ml to about 200 ng/ml, yet more typically from about 75 ng/ml to about 125 ng/ml, most typically at about 100 ng/ml.

This aspect of the present invention relies upon routine techniques in the field of cell culture. Suitable cell culture methods and conditions can be determined by those of skill in the art using known methodology (see, e.g., Freshney et al., CULTURE OF ANIMAL CELLS (3rd ed. 1994)). In general, the cell culture environment includes consideration of such factors as the substrate for cell growth, cell density and cell contract, the gas phase, the medium, and temperature.

Incubation of cells is generally performed under conditions known to be optimal for cell growth. Such conditions may include, for example, a temperature of approximately 37° C. and a humidified atmosphere containing approximately 5% $CO_2$. The duration of the incubation can vary widely, depending on the desired results. In general, incubation is preferably continued until the cells express suitable Proliferation is conveniently determined using $^3H$ thymidine incorporation or BrdU labeling.

Plastic dishes, flasks, or roller bottles may be used to culture cells according to the methods of the present invention. Suitable culture vessels include, for example, multi-well plates, petri dishes, tissue culture tubes, flasks, roller bottles, and the like.

Cells are grown at optimal densities that are determined empirically based on the cell type. Cells are typically passaged 12-5 times and discarded after 15 passages.

Cultured cells are normally grown in an incubator that provides a suitable temperature, e.g., the body temperature of the animal from which is the cells were obtained, accounting for regional variations in temperature. Generally, 37° C. is the preferred temperature for cell culture. Most incubators are humidified to approximately atmospheric conditions.

Important constituents of the gas phase are oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1-10% in the incubator. The preferred $CO_2$ concentration typically is 5%.

Defined cell media are available as packaged, premixed powders or presterilized solutions. Examples of commonly used media include MEM-α, DME, RPMI 1640, DMEM, Iscove's complete media, or McCoy's Medium (see, e.g., GibcoBRL/Life Technologies Catalogue and Reference Guide; Sigma Catalogue). Typically, MEM-α or DMEM are used in the methods of the invention. Defined cell culture media are often supplemented with 5-20% serum, typically heat inactivated serum, e.g., human, horse, calf, and fetal bovine serum. Typically, 10% fetal bovine serum is used in the methods of the invention. The culture medium is usually buffered to maintain the cells at a pH preferably from about 7.2 to about 7.4. Other supplements to the media typically include, e.g., antibiotics, amino acids, and sugars, and growth factors.

C. Detection of Osteogenesis

After administration of the compositions of the present invention in vivo or in vitro, induction of osteogenesis can be detected by detecting expression of osteoblast-specific proteins, detecting expression of bone-specific transcription factors, and detecting changes in bone density. Osteoblast-specific proteins include, for example, alkaline phosphatase (ALP), collagen type I, osteocalcin, and osteoponin (see, e.g., Olsen et al., *Annu. Rev. Cell. Dev. Biol.* 16:191 (2000)). Typically, expression of alkaline phosphatase is detected as an indicator of osteogenesis. Bone specific transcription factors include, for example, Cbfa1/Runx2, gsc, Dlx1, Dlx5, Msx1, Cart1, Hoxa1, Hoxa2, Hoxa3, Hoxb1, rae28, Twist, AP-2, Mf1, Pax1, Pax3, Pax9, TBX3, TBX4, TBX5, and Brachyury (see, e.g., Olsen et al, 2000 supra). Typically, expression of Cbfa1/Runx2 is detected as an indicator of osteogenesis.

1. Detection of Osteoblast-Specific Proteins

Expression of osteoblast-specific proteins may be detected by measuring the level of the osteoblast-specific protein or mRNA. The level of particular osteoblast-specific proteins can conveniently be measured using immunoassays such as immunohistochemical staining, western blotting, ELISA and the like with an antibody that selectively binds to the particular osteoblast specific proteins or a fragment thereof. Detection of the protein using protein-specific antibodies in immunoassays is known to those of skill in the art (see, e.g., Harlow & Lane, Antibodies: A Laboratory Manual (1988), Coligan, Current Protocols in Immunology (1991); Goding, Monoclonal Antibodies: Principles and Practice (2d ed. 1986); and Kohler & Milstein, Nature 256:495-497 (1975). For measurement of mRNA, amplification, e.g., PCR, LCR, or hybridization assays, e.g., northern hybridization, RNAse protection, dot blotting, are preferred. The level of protein or mRNA is detected, for example, using directly or indirectly labeled detection agents, e.g., fluorescently or radioactively labeled nucleic acids, radioactively or enzymatically labeled antibodies. These assays are well-known to those of skill in the art and described in, e.g., Ausubel, et al. ed. CURRENT PROTOCOLS IN MOLECULAR BIOLOGY (2001).

Typically, expression of the osteoblast specific-protein, alkaline phosphatase, is used to detect differentiated osteoblasts. Expression of alkaline phosphatase (ALP) is correlated with osteogenesis. ALP hydrolyzes inorganic pyrophosphates to phosphates and promotes the formation of hydroxyapatite crystals in bone matrix. Deactivating mutations of ALP cause osteomalacia, characterized by poorly mineralized bones and frequent bone factures, indicating that ALP plays a significant role in bone formation (see, e.g., Hessle et al., *Proc. Natl. Acad. Sci. USA*. 99:9445(2002)). ALP is a highly active and stable enzyme, making direct assays of its enzymatic activity convenient. In addition, direct histochemical staining of cells can conveniently be used to detect ALP.

a) Enzymatic Activity

For direct assays of ALP activity, cells are plated in 384-well plates and treated with an appropriate amount of a compound of Formula I (e.g., Compound A), either alone or with other growth factors (e.g., BMP-4) and then incubated at 37° C. in 5% $CO_2$. After an appropriate incubation time, the media is removed and lysis buffer is added into each well. After an appropriate incubation time in lysis buffer, alkaline phosphatase substrate solution (e.g., 2'-[2'-benzothiazoyl]-6'-hydroxybenzothiazole phosphate (BBTP)) is added to each well. After an appropriate incubation time at room temperature, the plates are read on a plate reader using methods known in the art.

b) Immunohistochemical Detection

For direct immunohistochemical staining of cells to detect ALP, cells are seeded in 96-well assay plates at a suitable density and treated with an appropriate amount of a compound of Formula I (e.g., Compound A), either alone or with other growth factors (e.g., BMP-4) for an appropriate time. Cells are then and fixed in a 10% formalin solution. The fixed cells are washed again and stained with a reagent specific for ALP (e.g., an antibody specific for ALP or a colorimetric ALP substrate) using methods known to those of skill in the art (see, e.g., Harlow & Lane, 1988, supra; Coligan, 1991, supra; Goding, 1986, supra; and Kohler & Milstein, 1975, supra). Photographic images of the cells are taken and ALP positive cells are counted manually from the images.

2. Detection of Bone-Specific Transcription Factors

Expression of bone-specific transcription factors can be detected using reporter gene assays. These assays are well known to those of skill in the art and are described in, e.g., Ausebel et al., supra. Expression of the bone specific transcription factor Cbfa1/Runx2 is typically used to detect osteogenesis. Cbfa1/Runx2 plays an essential role in osteoblast differentiation transgenic mice lacking the Cbfa1/Runx2 gene die shortly after birth due to loss in bone formation (see, e.g., Ducy et al., *Cell* 89:747 (1997) and Komori et al., *Cell* 89:755 (1997)).

Reporter genes such as, for example, chloramphenicol acetyltransferase, firefly luciferase, bacterial luciferase, or β-galactosidase can be used in the reporter gene assays. The reporter construct is typically transiently or stably transfected into a cell. The promoter region of the relevant gene is typically amplified by PCR appropriate primers. The resulting PCR product is inserted into a suitable cloning vector, amplified and sequenced. The resulting plasmid is digested with appropriate restriction enzymes and the resulting fragment is inserted into a vector comprising a reporter gene.

a) Transiently Transfected Cells

For reporter gene assays with transiently transfected cells, the cells are typically seeded in a 6-well plate at a density of 30,000 cells/well in 2 mL of growth medium an incubated overnight or for a suitable time. Plasmid DNA is transfected into the cells using a suitable transfection reagent. After 8 hours, the transfected cells are plated into 96-well assay plates (e.g., Corning) and treated with an appropriate amount of a compound of Formula I (e.g., Compound A). The cells are incubated for 4 days, then the reporter gene activity in the cells is assayed using methods known to those of skill in the art.

b) Stably Transfected Cells

For reporter gene assays with stably transfected cells, the cells are typically seeded in a 6-well plate at a density of 30,000 cells/well in 2 mL of growth medium an incubated overnight or for a suitable time. An appropriate amount of reporter plasmid and a vector comprising a selectable marker (e.g., an antibiotic resistance gene) are co-transfected into the cells using an appropriate transfection reagent. After an appropriate incubation time, cells are seeded in a 10 cm culture dish and an appropriate amount of antibiotic is added to the culture medium. Fresh antibiotic is added at appropriate intervals. The antibiotic resistant colonies are pooled to yield the stably transfected cells. The transfected cells are plated into 96-well assay plates (e.g., Corning) and treated with an appropriate amount of a compound of Formula I (e.g., Compound A). The cells are incubated for 4 days, then the reporter gene activity in the cells is assayed using methods known to those of skill in the art.

3. Detection of Bone Density

To assess the effect of the compositions of the present invention on bone density, a baseline measurement of bone density in an individual who will receive treatment may taken. Bone density is periodically measured at suitable intervals during and after administration of the compounds of Formula I, e.g., Compound A. Methods and devices for measuring bone density are well known in the art and are described in, e.g., U.S. Pat. Nos. 6,436,042; 6,405,068; 6,320,931; 6,302,582; 6,246,745; 6,230,036; 6,213,934; 6,102,567; 6,058,157; 5,898,753; 5,891,033; 5,852,647; 5,817,020; 5,782,763; 5,778,045; 5,749,363; 5,745,544; 5,715,820; 5,712,892; 5,572,998; and 5,480,439.

4. Administration of Differentiated Osteoblast Cells

Differentiated osteoblast cells can be administered to a subject by any means known to those of skill in the art. In one embodiment of the invention, differentiated osteoblast cells on an intact solid support (e.g., a three-dimensional matrix or a planar surface) can be administered to the subject, e.g., via surgical implantation. Alternatively, the differentiated osteoblast cells can be detached from the matrix, i.e., by treatment with a protease, before administration to the subject, e.g., intravenous, subcutaneous, or intraperitoneal.

In some embodiments of the present invention, mesenchymal stem cells are extracted from a human and subsequently contacted with a matrix for proliferation and differentiation into cells of an osteoblastic cell lineage. Cells can be extracted from the subject to be treated, i.e., autologous (thereby avoiding immune-based rejection of the implant), or can be from a second subject, i.e., heterologous. In either case, administration of cells can be combined with an appropriate immunosuppressive treatment.

Osteoblast cells differentiated according to the methods of the present invention may be administered to a subject by any means known in the art. Suitable means of administration include, for example, intravenous, subcutaneous, intraperitoneal, and surgical implantation.

The cells may be in formulations suitable for administration, such as, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can be prepared from sterile powders, granules, and tablets.

For surgical implantation, differentiated cells are typically left on an intact solid support, e.g., a three-dimensional matrix or planar surface. The matrix or planar surface is surgically implanted into the appropriate site in a subject. For example, a patient needing a bone graft can have differentiated cells on an intact solid support surgically implanted.

In determining the effective amount of the cells to be administered in the treatment or prophylaxis of conditions owing to diminished or aberrant osteoblasts, the physician evaluates cell toxicity, transplantation reactions, progression of the disease, and the production of anti-cell antibodies. For administration, osteoblast cells differentiated according to the methods of the present invention can be administered in an amount effective to provide osteoblasts to the subject, taking into account the side-effects of the osteoblasts at various concentrations, as applied to the mass and overall health of the patient. Administration can be accomplished via single or divided doses.

EXAMPLES

The following examples are offered to illustrate, but not to limit, the claimed invention.

Example 1

Synthesis and Characterization of Compound A

The phosphine ligand for the Pd-catalyzed coupling was purchased from Strem Chemicals. All the other chemicals were purchased from Aldrich.
Solid Phase Synthesis The C6 position of 2,6-dichloro-9-substituted-purine was substituted by suspending (4-formyl-3,5-dimethoxyphenoxy)methyl polystyrene resin (PAL-resin) in dimethylformamide (DMF). A suitably substituted aniline, acetic acid and sodium triacetoxyborohydride were then added to the solution. The mixture was shaken gently at room temperature for 12 hours. The resulting aniline bound resin was then washed with DMF, methanol and dichloromethane. The aniline bound resin was then reacted with 2,6-dichloro-9-substituted-purine and diisopropylethylamine in 1-butanol at 80° C. for 12 hours. The resulting resin was then washed as described above to afford the 2-chloro-6-resin bound aniline-9-substituted purine.

The C2 position of the purine ring was subsequently substituted by mixing the purine bound PAL resin with a-

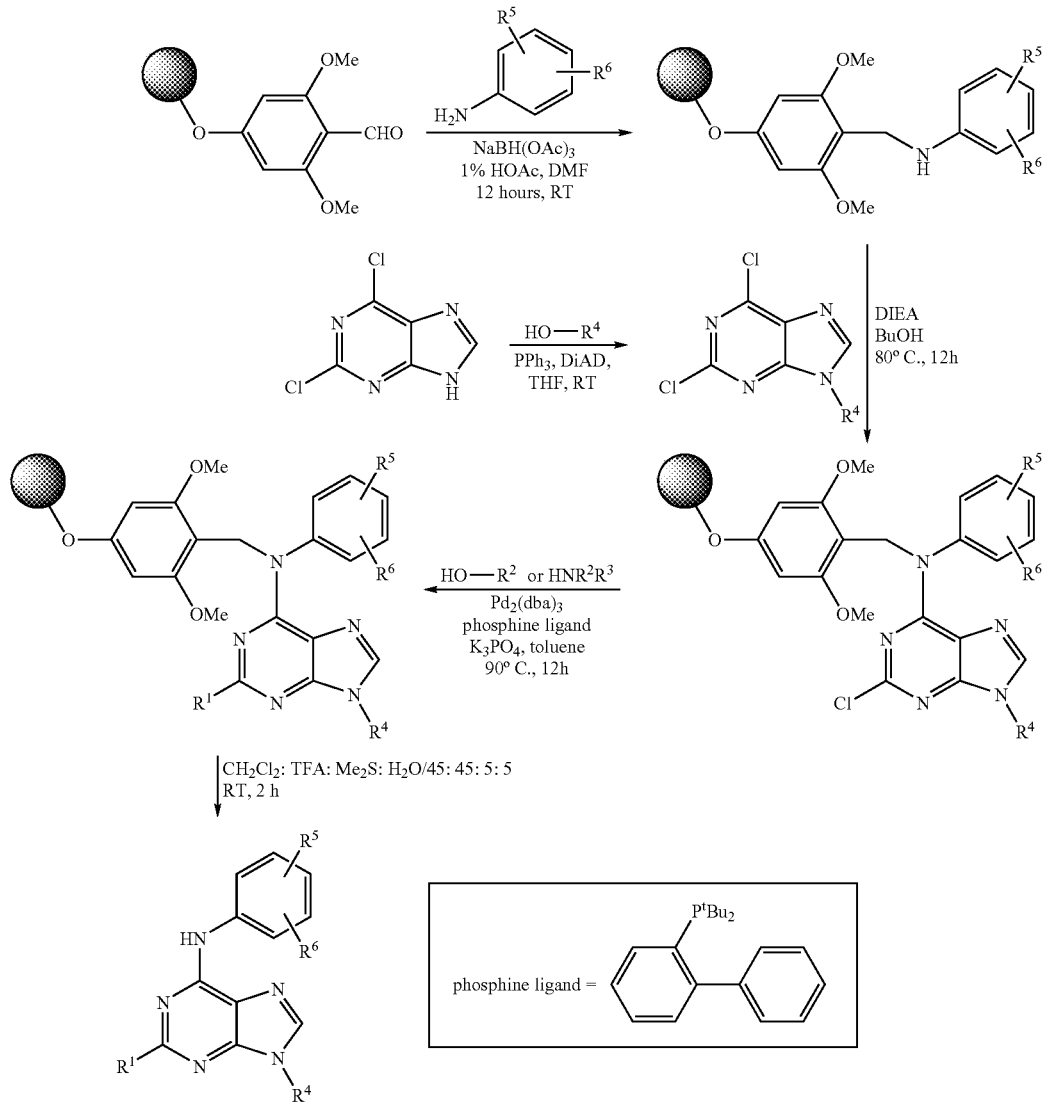

suitable amine or aryl alcohol, Pd$_2$(dba)$_3$, 2-(di-t-butylphosphino)biphenyl and K$_3$PO$_4$ in a 10 mL flame-dried Schlenk flask. The flask was then evacuated and refilled with argon, and anhydrous toluene was added. The mixture was heated at 80° C. for 12 hours. The resulting resin was then washed as described above and cleaved with CH$_2$Cl$_2$:TFA:Me$_2$S:H$_2$O/45:45:5:5 at room temperature for 2 hours. The solution was collected and dried in vacuo to afford the desired crude product. The crude product was then purified using preparative HPLC using H$_2$O (with 0.1% TFA) and acetonitrile (MeCN) as solvents. A linear gradient of 5% to 95% MeCN over 5 min was used. The corresponding peak was collected and lyophilized to afford the pure desired 2,6,9-substituted purine.

Synthesis of 2-(1-Naphthoxy)-6-(4-morpholinoanilino)-9-cyclohexylpurine (Compound A)

PAL-resin (1 g, 1.1 mmol) was suspended in DMF (4 mL) and 4-morpholinoaniline (196 mg, 5.5 mmole), acetic acid (0.65 mL, 1.13 mmol) and sodium triacetoxyborohydride (720 mg, 3.4 mmol) were then added into the solution. The mixture was shaken gently at room temperature for 12 hours. The resulting resin was then washed with DMF (10 mL, 3 times), methanol (10 mL, 3 times) and dichloromethane (10 mL, 3 times). The aniline bound resin was then reacted with 2,6-dichloro-9-cyclohexylpurine (598 mg, 2.2 mmole) and diisopropylethylamine (0.5 mL, 3 mmol) in 1-butanol (5 mL) at 80° C. for 12 hours. The resulting resin was then washed as described above.

Purine bound PAL resin (100 mg, 0.1 mmol) was mixed with 1-naphthol (72 mg, 0.5 mmol), Pd$_2$(dba)$_3$ (6.4 mg, 0.007 mmol), 2-(di-t-butylphosphino)biphenyl (8.3 mg, 0.028 mmol) and K$_3$PO$_4$ (148 mg, 0.7 mmol) in a 10 mL flame-dried Schlenk flask. The flask was then evacuated and refilled with argon, and anhydrous toluene (1 mL) was added. The mixture was heated at 80° C. for 12 hours. The resulting resin was then washed as described above and cleaved with CH$_2$Cl$_2$:TFA:Me$_2$S:H$_2$O/45:45:5:5 (0.5 mL) at room temperature for 2 hours. The solution was collected and dried in vacuo to afford the desired crude product. The crude product was then purified using preparative HPLC using H$_2$O (with 0.1% TFA) and MeCN as solvents. A linear gradient of 5% to 95% MeCN over 5 min was used; the desired compound has the retention time of 3.9 min. The corresponding peak was collected and lyophilized to yield pure 2-(1-Naphthoxy)-6-(4-morpholinoanilino)-9-cyclohexylpurine (light yellow powder, 24 mg, overall 50% yield). $^1$H NMR (400 MHz, CDCl$_3$): δ (Ppm) 1.34 (m, 1H), 1.58 (m, 2H), 1.75 (m, 2H), 1.85 (m, 1H), 2.01 (m, 2H), 2.33 (m, 2H), 3.21 (t, 4H, J=4.8 Hz), 3.99 (t, 4H, J=4.9 Hz), 4.67 (m, 1H), 6.73 (d, 2H, J=9.1 Hz), 7.16 (2H, J=9.1 Hz), 7.33 (d, 1H, J=7.4 Hz), 7.44 (t, 1H, J=8.3 Hz), 7.54 (m, 2H), 7.88 (d, 1H, J=8.3 Hz), 7.93 (d, 1H, J=8.2 Hz), 8.27 (s, 1H), 10.22 (s, 1H). High Resolution Mass Spectrometry (MALDI-FTMS): calculated [MH$^+$] (C$_{31}$H$_{33}$N$_6$O$_2$) 521.2665, found 521.2670; calculated [MNa$^+$] (C$_{31}$H$_{32}$N$_6$NaO$_2$) 543.2484, found 543.2488.

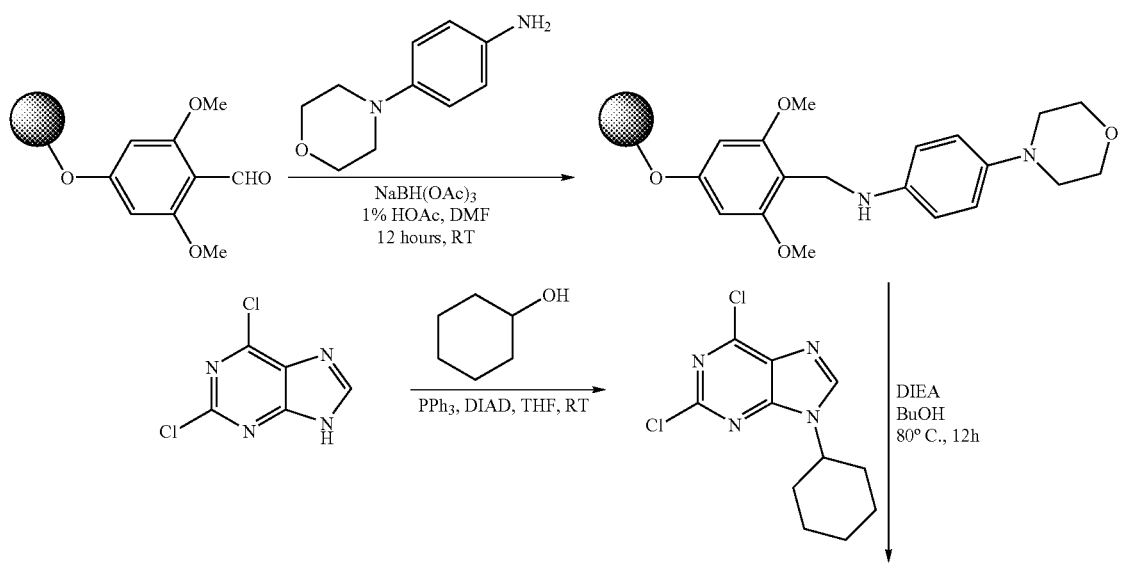

Scheme 2: Solid-phase synthesis of Compound A

-continued
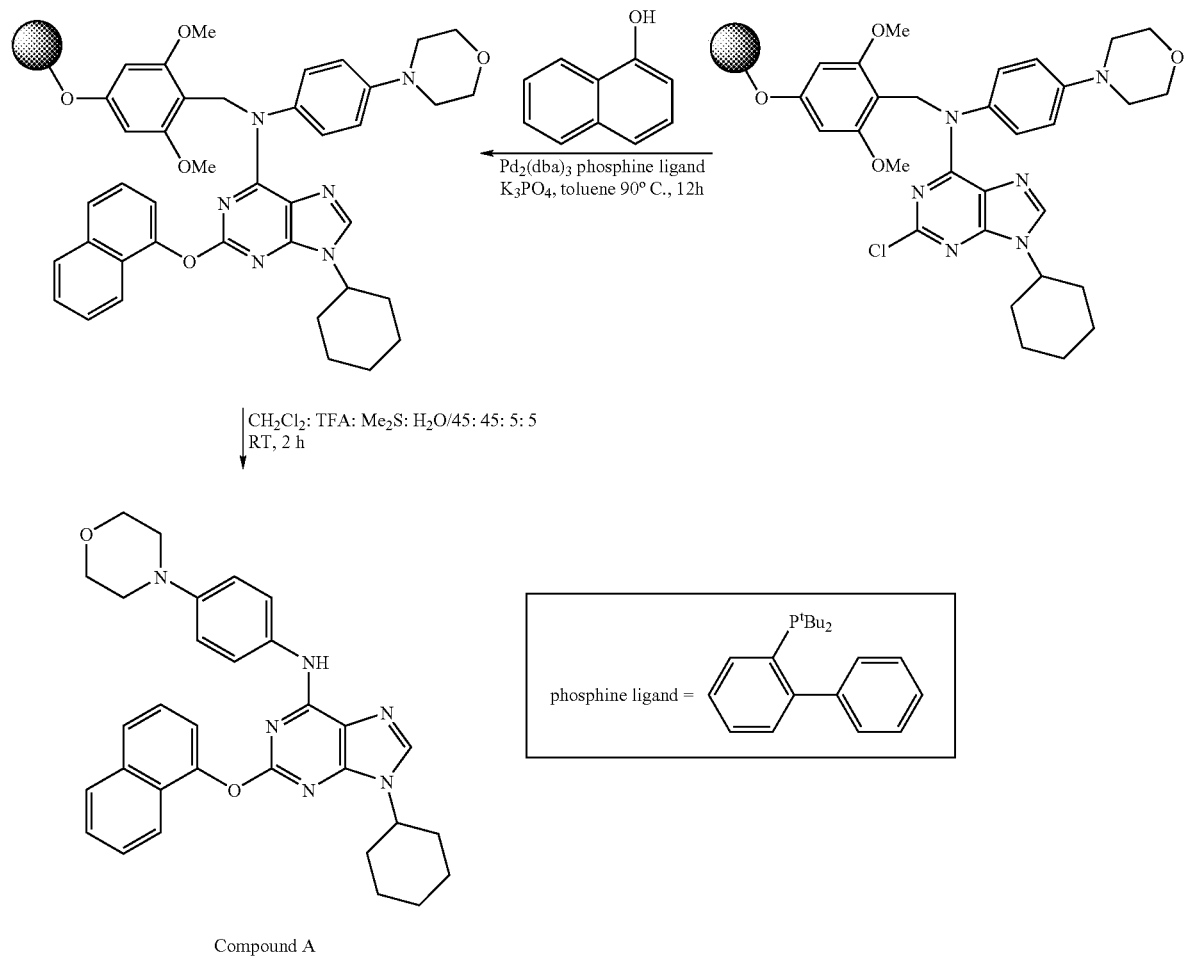
Compound A
Solution Phase Synthesis
Scheme 3: Solution phase synthesis of 2, 6, 9-substituted purines.
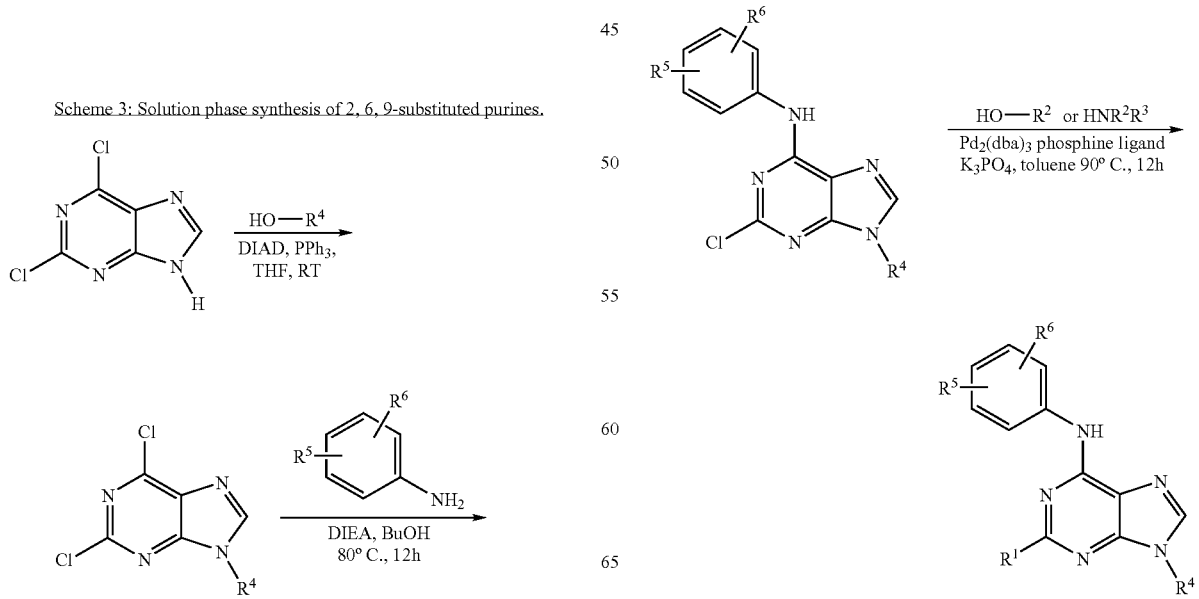

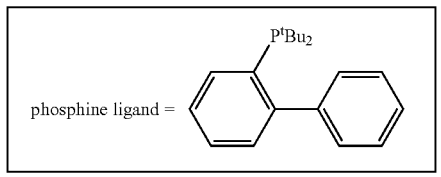

2,6-dichloropurine was reacted with diisopropylazodicarboxylate (DIAD), triphenylphosphine and a suitable alcohol in anhydrous THF at −78° C. The reaction mixture was warmed up to room temperature slowly to yield the 2,6-dichloro-N-9-substituted purine. Sequentially, the 2,6-dichloro-9-substituted purine was then heated with a suitably substituted aniline and diisopropylethylamine (DIEA) at 80° C. for 12 hours to yield 6-anilino-2-chloro-9-substituted purine. This compound was then reacted with a suitable substituted amine or arylalcohol along with a palladium catalyst to afford the desired 2,6,9-substituted purines.

Example 2

Cell Culture and Osteogenesis Detection Assays

Cell Culture: Mouse embryonic mesoderm fibroblasts C3H10T1/2 cells were obtained at the 10th passage from ATCC. Cells between the 12th and 15th passages were used in these experiments. Cells beyond 15th passage were discarded. Mouse embryonic mesoderm fibroblasts C3H10T1/2 cells and mouse pre-osteoblasts MC3T3-E1 cells (from German collection of microorganisms and cell cultures) were cultured at 37° C. in 5% $CO_2$ in MEM-α media (Gibco) supplemented with 10% heat inactivated FBS (Gibco), 50 U/mL penicillin and 50 μg/mL of streptomycin (Gibco). When cells were 80% confluent, they were split a 1:5. Mouse pre-adipocytes 3T3-L1 cells (from ATCC) and mouse myoblasts C2C12 cells (from ATCC) were cultured at 37° C. in 5% $CO_2$ in DMEM (Gibco) supplemented with 10% heat inactivated FBS (Gibco), 50 U/mL penicillin and 50 g/mL of streptomycin (Gibco).

Alkaline Phosphatase Assay: C3H10T1/2 cells were expanded in T175 flasks; cells at the 13th passage were detached by trypsin/EDTA and diluted in the growth media. The resulting cell suspension was then plated into black clear bottom 384-well plates (Greiner) with 2500 cells/well in 100 μL growth media using a Multi-drop™ liquid delivery system (Titertek Instruments). After an overnight incubation, cells were attached to the bottom of the wells. A stock solution of Compound A in DMSO (500 nL) was delivered into corresponding well using a Mini Trak™ multiposition dispenser system (Packard BioScience) to make the final concentration of 5 μM of each compound. Cells were then incubated at 37° C. in 5% $CO_2$. After 4 days, the media was removed and 10 μL of Passive Lysis Buffer (Promega) was added into each well. After 5 min, 10 μL of alkaline phosphatase substrate solution (1 mM in pH 10 buffer, 2'-[2'-benzothiazoyl]-6'-hydroxybenzothiazole phosphate (Promega) was added to each well. After a 15 minute incubation at room temperature, the plates were read on an Acquest high-throughput plate reader (Molecular Devices) using the manufacturer's protocol.

Cbfa1/Runx2 Reporter Gene Assay: The murine Cbfa1/Runx2 gene promoter region (1818 bp) was amplified by PCR from mouse genomic DNA library (Clontech) using the following primers:

5'-ACGCGTAAGAATCTTATGAACATGATTTCA    (SEQ ID NO:1)
and
5'-CTCGAGTCACACAATCCAAAAAAGCAAAA    (SEQ ID NO:2)

The resulting PCR product was inserted into Topo cloning vector (Invitrogen), amplified and sequenced. The resulting plasmid was digested with restriction enzymes Mlu and XhoI (New England Biolab) and the 1.8 kb fragment was inserted into the Mlu/XhoI cloning sites in pGL3-BV luciferase reporter vector (Promega). For transient transfection assays, cells were seeded in a 6-well plate at a density of 30,000 cells/well in 2 mL of growth medium. After an overnight incubation, the cells reached 80% confluency. Plasmid DNA (1 μg) was transfected into cells using 3 μL of Fugene 6 transfection reagent (Roche) using the manufacturer's protocol. After 8 hours, the transfected cells were plated into 96-well assay plates (Corning) and treated with 300 ng/mL of recombinant human bone morphogenetic protein 4 (BMP-4) (Sigma), 1% DMSO (Sigma) or different concentrations of Compound A (dissolved in DMSO). The cells were incubated for 4 days, then the luciferase activity in the cells was assayed using the Bright-Glo luciferase assay kit (Promega) using the manufacturer's protocol. Luminescence signals were detected by Acquest AD (Molecular Devices) plate reader. Due to the low transfection efficiency of MC3T3-E1 cells, the Cbfa1/Runx2 reporter assay was carried out with stably transfected MC3T3-E1 cells. Generally, MC3T3-E1 cells were plated in a 6-well plate at 30,000 cells/well. After an overnight incubation, 1 μg of reporter plasmid and 0.2 μg of pCMV-Tag2B vector comprising a neomycin resistance gene were co-transfected into MC3T3-E1 cells using 3.6 μL of Fugene 6 transfection reagent (Roche) following the manufacturer's protocol. After 8 hours, cells were detached by treatment with trypsin/EDTA and seeded in a 10 cm culture dish. After the cells attached to the dish, 200 μg/mL of G418 (Gibco) was added to the culture medium. Fresh G418 was added every 3 days. After 14 days, the neomycin resistant colonies were pooled to yield the stably transfected MC3T3-E1 cells.

Histochemical Staining for Endogenous Alkaline Phosphatase Expression: C3H10T1/2 cells were seeded in 96-well assay plates (Corning) at a density of 10,000 cells/well, and treated with 300 ng/mL of BMP-4, 1% DMSO, 2 μM of Compound A, or 100 ng/mL of BMP and 1 μM of Compound A for 4 days. The cells were then washed 3 times with 200 μL PBS and fixed by a 15 minute incubation in a 10% formalin solution (Sigma). The fixed cells were washed again with 3 times with 200 μL PBS and stained with the Alkaline Phosphatase Staining Kit 86R (Sigma Diagnostics) using the manufacturer's protocol. The images were taken on a Nikon Eclipse TE300 microscope, and ALP positive cells were counted manually from the images.

Example 3

Identification of Compound A as a Compound with Osteogenesis Inducing Activity

A heterocycle combinatorial library of approximately 50,000 compounds with purine, pyrimidine, quinazoline, pyrazine, phthalazine, pyrazine and quinoxaline-based scaffolds was screened to identify small molecules with osteogenesis inducing activity (see, e.g., Ding et al., *J. Am. Chem. Soc.* 124:1594(2002);Gray et al., *Science* 281:533 (1998);

Rosania et al. *Nat. Biotechnol.* 18:304 (2000); and Rosania et al., *Proc. Natl. Acad. Sci. USA.* 96:4797 (1999). One 2,6,9-trisubstituted purine was found to have significant activity in the ALP enzymatic assay. This compound, which has morpholinoaniline substitution at the C6 position of purine nucleus, was named Compound A. Further studies indicated that the EC50 for Compound A is 1 µM in C3H10T1/2 cells; moreover, this compound can lead to greater than a 50 fold increase in ALP after treatment for 4 days as compared with 1% DMSO treatment, and is more effective than BMP-4 in inducing the expression of ALP (FIG. 1).

Example 4

Compound A is a Potent Inducer of Osteogenesis in Multipotent C3H10T1/2 Cells

Mouse embryonic mesoderm fibroblast C3H10T1/2 cells were used for this study. C3H10T1/2 cells, like MSCs, are multipotent mesenchymal progenitor cells which can differentiate into various mesenchymal cells and have been widely used as a model system for studies of osteoblast differentiation (see, e.g., 3. Taylor, et al., *Cell* 17:771 (1979) and Aubin and Liu, F., PRINCIPLES OF BONE BIOLOGY; Bilezikian, et al. ed.; Academic Press, San Diego: pp.51-67). Upon treatment with bone morphogenetic protein 4 (BMP-4), C3H10T1/2 cells differentiate into osteoblasts (see, e.g., Piccolo, et al., *Cell* 86:589 (1996)).

C3H10T1/2 cells were treated with DMSO (control), BMP-4(300 ng/mL), BMP-4 (100 ng/mL) and Compound A (1 µM), or 0.5 µM, 1 µM, 1.2 µM, 1.5 µM, 1.8 µM, 2 µM, 5 µM, or 10 µM Compound A. Alkaline phosphatase (ALP) activity was measured as described in Example 2 above, after two, four, and six days of treatment. The results are shown in FIG. 1.

Example 5

Compound A is a Potent Inducer of Osteogenesis in C3H10T1/2 cells, 3T3-L1, MC-3T3E1 Cells, and C2C12 Cells C3H10T1/2 cells, 3T3-L1, MC-3T3E1 cells, and C2C12 cells were treated with DMSO (control), BMP-4(300 ng/mL), BMP-4 (100 ng/mL) and Compound A (1 µM), or 1 µM, 2 µM, or 10 µM Compound A. Cbfa1/Runx2 reporter gene activity was assayed as described in Example 2 above after four days of treatment.

Figure 2:
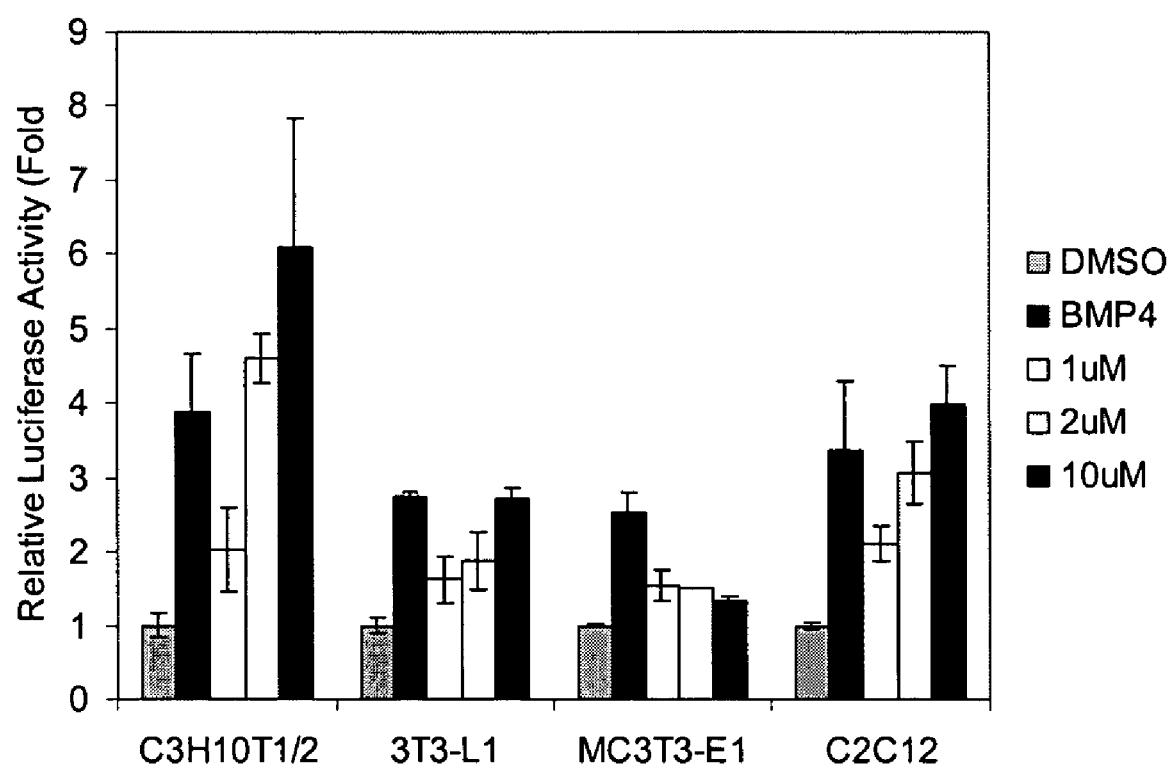
FIG. 2 illustrates the results demonstrating that Compound A is a potent inducer of osteogenesis in C3H10T1/2 cells, 3T3-L1, MC-3T3E1 cells, and C2C12 cells. The cells were treated with DMSO alone (control); BMP-4 alone (300 ng/mL); BMP-4 (100 ng/mL) and Compound A (1 µM); or 1 µM, 2 µM, or 10 µM Compound A alone. Cbfa1/Runx2 reporter gene activity was assayed after four days of treatment.

Treatment of C3H10T1/2 cells with Compound A for 4 days led to a more than 6 fold increase in the reporter activity in transient transfection experiments indicating Cbfa1/Runx2 gene is up-regulated. This result is consistent with the differentiation of C3H10T1/2 cells into an osteoblast lineage. These results are shown in FIG. 2.

Mouse MC3T3-E1 cells are progenitor cells committed to an osteoblast lineage. Both BMP-4 and Compound A promote the terminal differentiation of MC3T3-E1 cells. Since MC3T3-E1 cells already have high levels of endogenous Cbfa1/Runx2, slight up-regulation of this gene may be sufficient to promote terminal differentiation (see, e.g., Xiao et al., *J. Cell. Biochem.* 74:596 (1999) and Wang et al., *J. Bone. Miner. Res.* 14:893 (1999)). The change of Cbfa1/Runx2 reporter activity in stably transfected MC3T3-E1 cells is not dramatic when treated with Compound A.

Example 6

Figure 3:
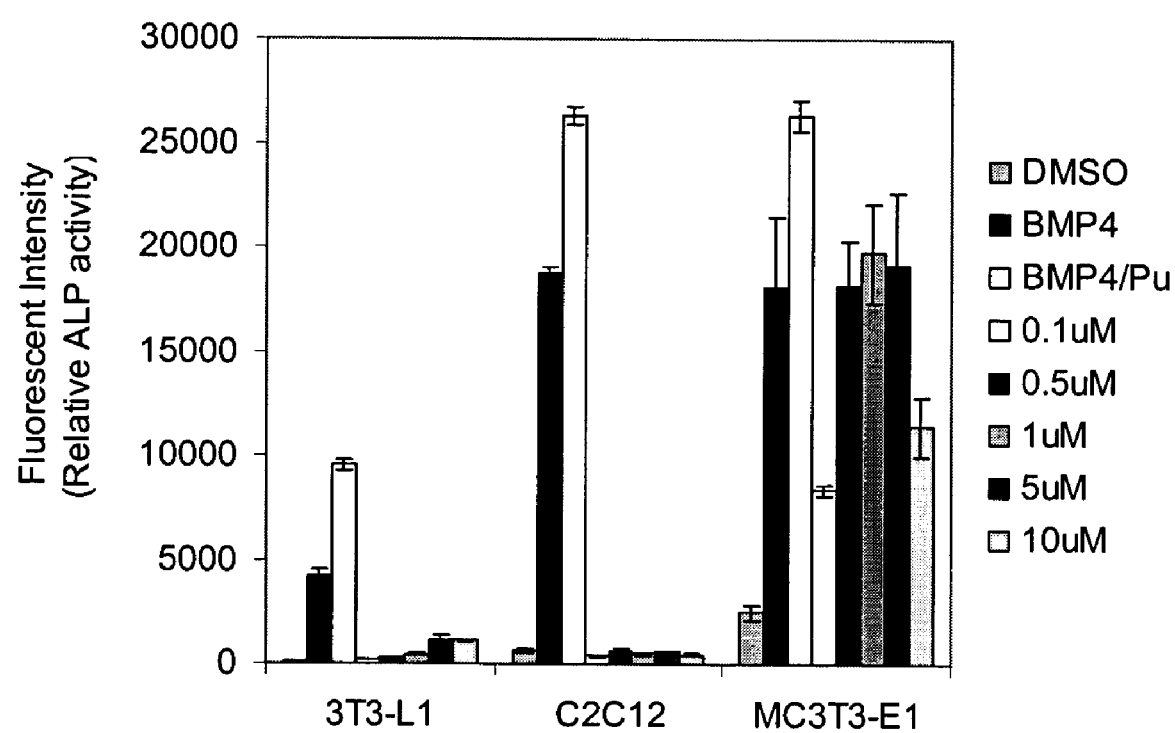
FIG. 3 illustrates results demonstrating that Compound A is a potent inducer of osteogenesis in multipotent 3T3-L1 cells, C2C12 cells, and MC-3T3E1 cells. The cells were treated with DMSO alone (control); BMP-4 alone (300 ng/mL); BMP-4 (100 ng/mL) and Compound A (1 µM); or 0.1 µM, 0.5 µM, 1 µM, 5 µM, or 10 µM Compound A alone. ALP activity was measured after four days of treatment.

Compound A is a potent inducer of osteogenesis in 3T3-L1 Cells, C2C12 Cells, and MC-3T3E1 Cells 3T3-L1 cells, C2C12 cells, and MC-3T3E1 cells were treated with DMSO (control), BMP-4(300 ng/mL), BMP-4 (100 ng/mL) and Compound A (1 µM), or 0.1 µM, 0.5 µM, 1 µM, 5 µM, or 10 µM Compound A. ALP activity was measured as described in Example 1 above, after four days of treatment. The results are shown in FIG. 3.

Example 7

Histochemical Staining of ALP Expression in C3H10T1/2 Cells Shows that Compound A is a Potent Inducer of Osteogenesis C3H10T1/2 cells were treated with DMSO (a), 300 ng/mL of BMP-4 (b), 2 µM of Compound A (c), and 100 ng/mL of BMP and 1 µM of Compound A (d) for 4 days and stained for ALP activity. ALP positive cells were stained red and the cell nuclei were stained blue.

Histochemical staining of endogenous ALP indicated that more than 80% of the cells expressed ALP after Compound A treatment (2 µM for 4 days), while only 40% of BMP-4 treated cells stained positive for ALP. Interestingly, although fewer cells were induced by BMP-4, those induced cells had higher expression level of ALP compared to cells treated with Compound A. Our observations suggest that Compound A induces the majority of the cell population to commit into an osteoblast lineage, while BMP-4 may be more potent in promoting the maturation of osteoblasts. Compound A also showed a synergistic effect with BMP-4 in inducing the differentiation of C3H10T1/2 cells. When cells were treated with both BMP-4 and Compound A, the induction for ALP activity was approximately 3 fold greater than the simple additive effect of the individual molecules, suggesting that Compound A does not act as a BMP-4 analogue.

Example 8

Compound A can Induce Transdifferentiation of Non-Osteoblast Lineage Cells into Osteoblasts 3T3-L1 pre-adipocyte cells, which are progenitor cells committed to an adipocyte lineage, can be transdifferentiated into osteoblast lineage when treated with Compound A and BMP-4. Compound A induces Cbfa1/Runx2 expression in pre-adipocyte cells, and increases the ALP level 9 fold at an optimal concentration of 5 µM, while BMP-4 induces ALP expression more than 40 fold. Compound A (1 µM) and BMP-4 (100 ng/mL) together increase ALP activity more than 90 fold in 3T3-L1 cells (FIG. 2). Similarly, C2C12 cells, which are progenitor cells committed to a skeletal muscle lineage, can be induced by Compound A to express the Cbfa1/Runx2 gene (FIG. 2). This observation is consistent with a previous report that transient up-regulation of Cbfa1/Runx2 is required, but not sufficient, to transdifferentiate C2C12 cells into osteoblasts(see, e.g., Lee et al., *J. Cell. Biochem.* 73:114 (1999)).

Example 9

Morphology of C3H10T1/2 Cells and C2C12 Cells after Treatment with Compound A C3H10T1/2 cells were treated with DMSO (1%) and Compound A (purmorphamine) (2 µM) for 4 days. C2C12 cells were treated with DMSO (1%), Compound A (purmorphamine) (2 µM) or BMP-4 (300 ng/mL) for 4 days. The morphology of the cells was examined under light microscopy. The morphology of the mouse embryonic mesoderm fibroblast C3H10T1/2 cells treated with Compound A changed from fibroblast (long and spindle-shaped) to osteocyte (small and round).

Example 10

Compound A is a Potent Inducer of Osteogenesis

Figure 4:
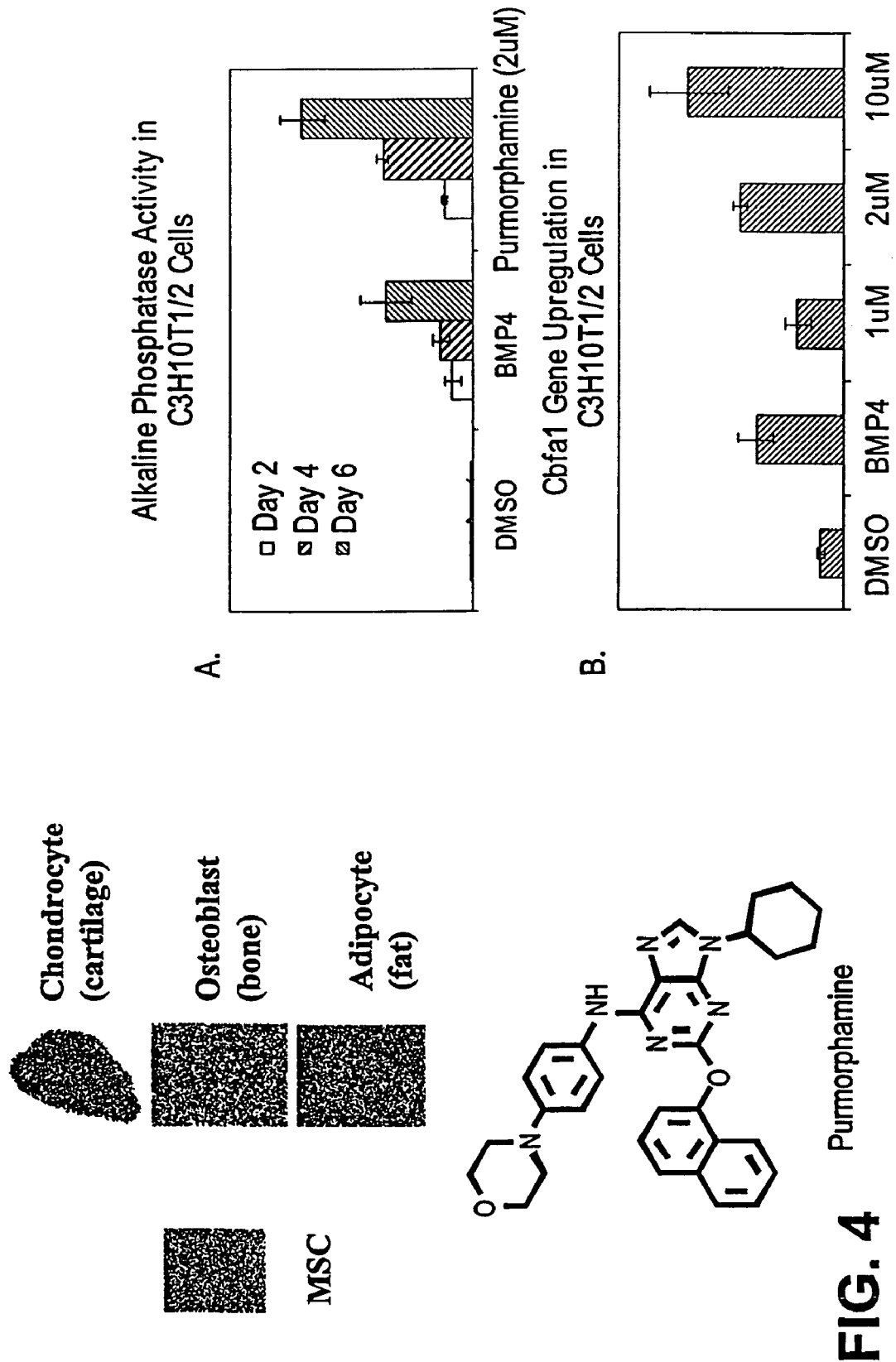
FIG. 4 illustrates that Compound A (i.e., purmorphamine) is a potent inducer of osteogenesis activity in mesenchymal (MSC) progenitor cells.

C3H10T1/2 cells were treated with DMSO alone (control); BMP-4 alone; and Compound A alone (2 µM). Alkaline phosphatase (ALP) activity was measured after two, four, and six days of treatment. FIG. 4A illustrates results demonstrating that Compound A is a potent inducer of osteogenesis in multipotent C3H10T1/2 cells.

FIG. 4B illustrates that Compound A induces Cbfa1 gene upregulation in C3H10T1/2 cells, indicating that Compound A induces the differentiation of C3H10T1/2 cells into cells of an osteoblast lineage.

Example 11

Figure 5:
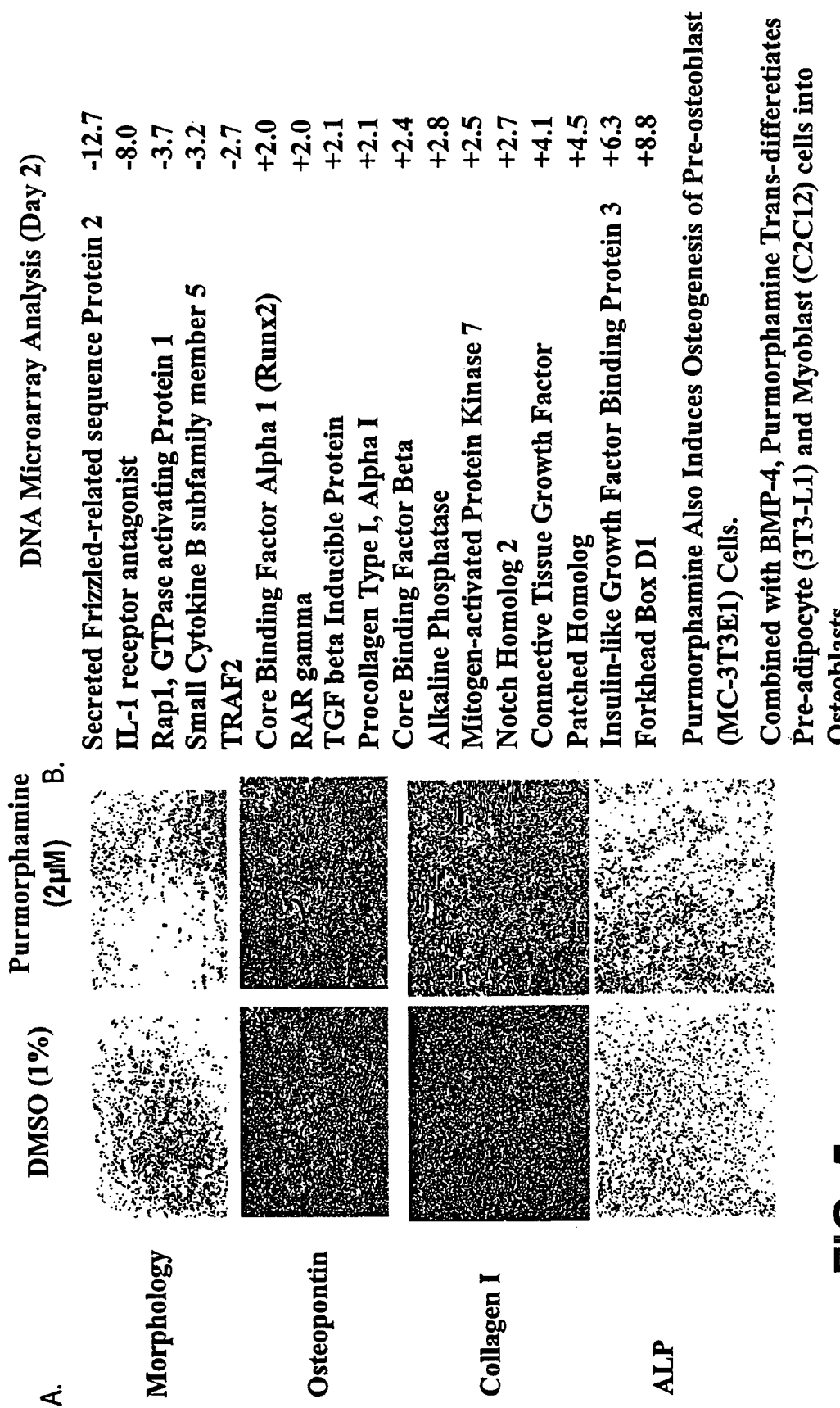
FIG. 5 illustrates morphological and transcriptional analysis of osteogenesis induced by Compound A.

Morphological and Transcriptional Analysis of Osteogenesis Induced by Compound A FIG. 5 illustrates morphological and transcriptional analysis of osteogenesis induced by Compound A. FIG. 5A indicates that Compound A induces expression of the following proteins: alkaline phosphatase, collagen type I and osteoponin, all of which indicate that osteogenesis is induced by Compound A. In addition, FIG. 5B sets forth a DNA microarray analysis indicating that Compound A induces expression of a number of transcription factors and proteins.

Example 12

Analysis of Additional Compounds for Osteogenesis-Inducing Activity

Additional compounds of Formula I were synthesized and tested for osteogenesis inducing activity using the alkaline phophastase assays and Cbfa1/Runx2 reporter gene assays described in Example 2, above.

For the compounds tested, $R^1$ was

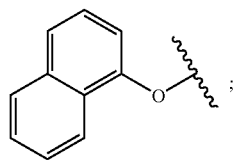

$R^5$ was H, $R^6$ was morpholine and the substiuent at $R^4$ was varied.

Typical $EC_{50}$ about 1 µM, 2 µM, 2.5 µM, 5 µM, 7 µM, or 10 µM.

The foregoing examples unequivocally establish that the compounds of the present invention (such as Compound A) induce osteogenesis of pre-osteoblast cells (such as MC-3T3E1 cells). In addition, combined with BMP-4, the compounds of the present invention (such as Compound A) transdifferentiate pre-adipocyte (such as 3T3-L1 cells) and myoblast (such as C2C12) cells into osteoblasts.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula I:

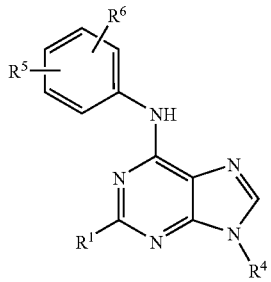

wherein:

$R^1$ is a member selected from the group consisting of hydrogen, halogen and —L—$R^2$;

L is a member selected from the group consisting of —O— and —N$R^3$—, wherein $R^3$ is H, or $R^3$ is optionally taken together with $R^2$ and the nitrogen to which both are attached to form a heterocycloalkyl, optionally substituted with $C_{1-4}$alkyl;

$R^2$ is a member selected from the group consisting of $C_{1-4}$alkyl, and aryl-$C_{0-2}$alkyl, substituted with 0-2 $R^{2a}$ groups that are independently selected from the group consisting of halogen, $C_{1-4}$alkyl, $C_{1-4}$alkoxy, —N($R^{2b}R^{2b}$), —SO$_2$N($R^{2b}R^{2b}$), —C(O)N($R^{2b}R^{2b}$) and —O-aryl, or when said $R^{2a}$ groups are on adjacent ring atoms they are optionally taken together to form a member selected from the group consisting of —O—(CH$_2$)$_{1-2}$—O—, —O—C(CH$_3$)$_2$CH$_2$— and —(CH$_2$)$_{3-4}$—;

each $R^{2b}$ group is a member that is independently selected from the group consisting of hydrogen and $C_{1-4}$alkyl;

$R^4$ is a member selected from the group consisting of $C_{1-4}$alkyl, $C_{3-8}$cycloalkyl, hydroxy-$C_{1-4}$alkyl, aryl-$C_{0-3}$alkyl, substituted with 0-2 $R^{4a}$ groups, cyclohexylmethyl and

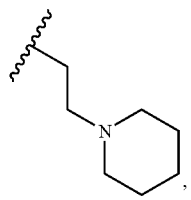

optionally substituted with $C_{1-4}$alkyl;

each $R^{4a}$ group is a member independently selected from the group consisting of hydrogen, halogen, $C_{1-4}$alkyl, $C_{1-4}$alkoxy, and aryl, or when said $R^{4a}$ groups are on adjacent ring atoms they are optionally taken together to form —O—$(CH_2)_{1-2}$—O—;

$R^5$ is hydrogen and $R^6$ is —$N(R^7R^8)$, or when $R^5$ and $R^6$ are on adjacent ring atoms they are optionally taken together to form —O—$(CH_2)_{1-2}$—O—;

$R^{7a}$ and $R^8$ are taken together with the nitrogen to which they are attached to form a heterocycloalkyl, optionally substituted with $C_{1-4}$alkyl; and all pharmaceutically acceptable salts and hydrates thereof.

2. A compound of claim 1, wherein:
$R^1$ is a member selected from the group consisting of:

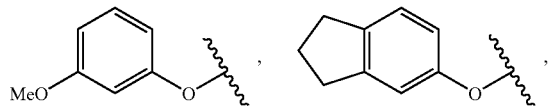
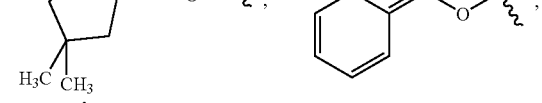
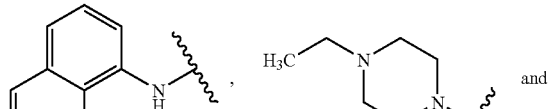
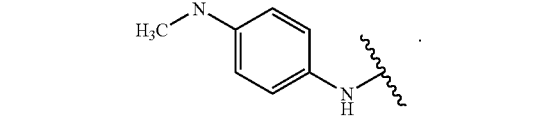

3. A compound of claim 1, wherein:
$R^1$ is

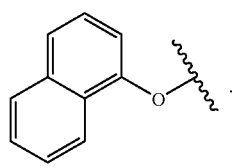

4. A compound of claim 1, wherein:
$R^4$ is a member selected from the group consisting of:

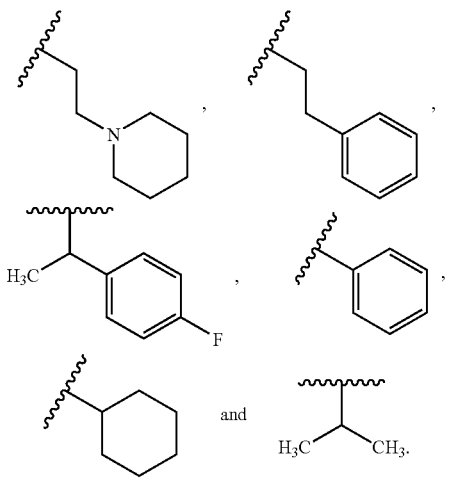

5. A compound of claim 1, wherein:
$R^4$ is cyclohexyl.

6. A compound of claim 1, wherein:
$R^5$ is H and $R^6$ is morpholine.

7. A compound of claim 1, wherein:
$R^1$ is

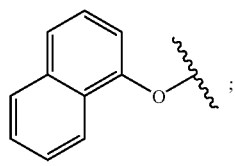

$R^5$ is H; and
$R^6$ is morpholine.

8. A compound having the formula:

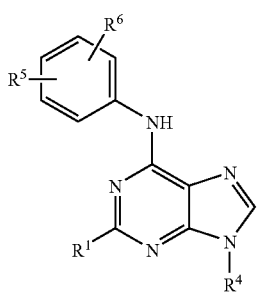

wherein:
$R^1$ is

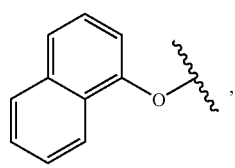

$R^5$ is H;
$R^6$ is morpholine; and
$R^4$ is a member selected from the group consisting of:
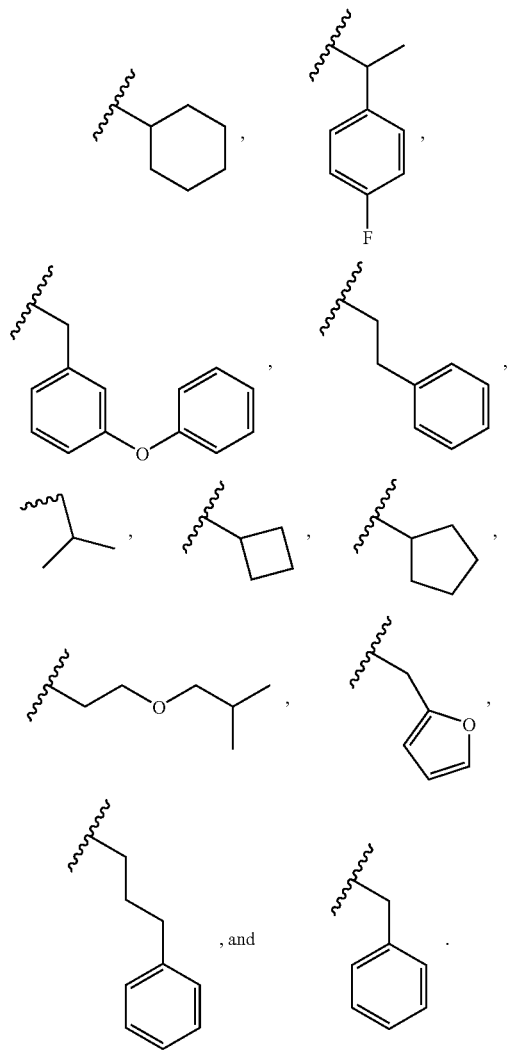
9. A compound selected from the group consisting of:
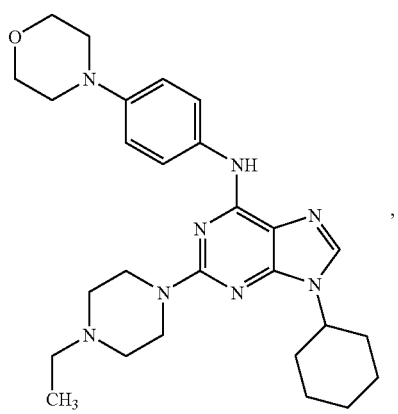
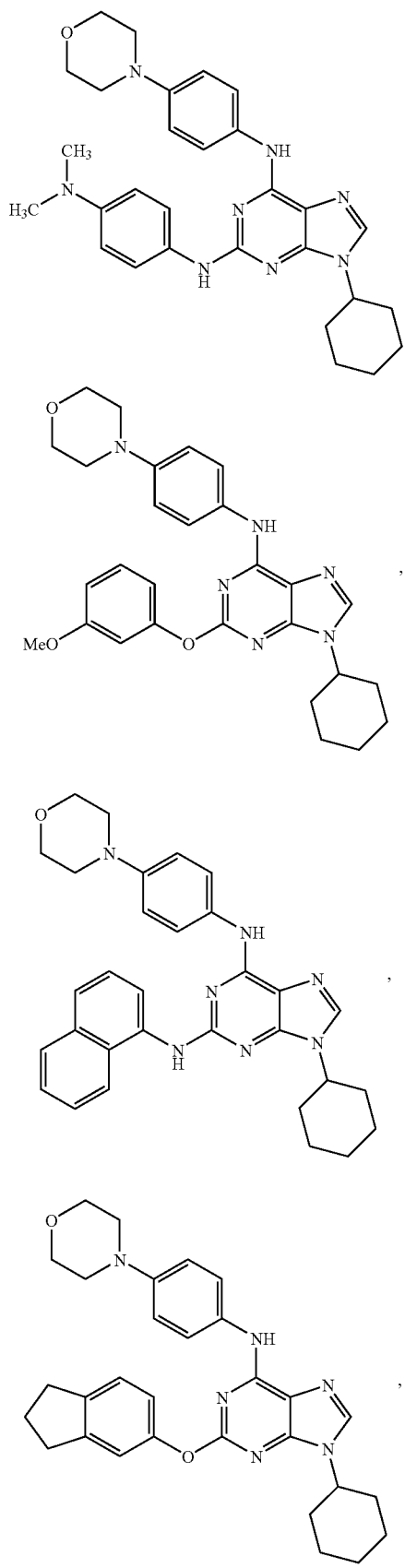

-continued
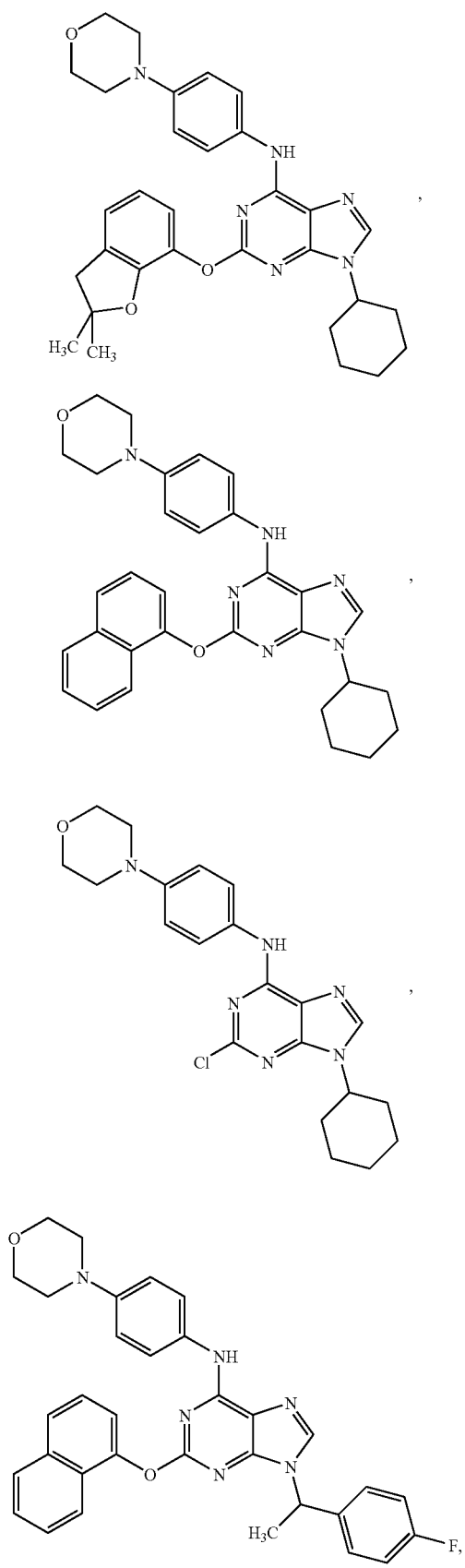
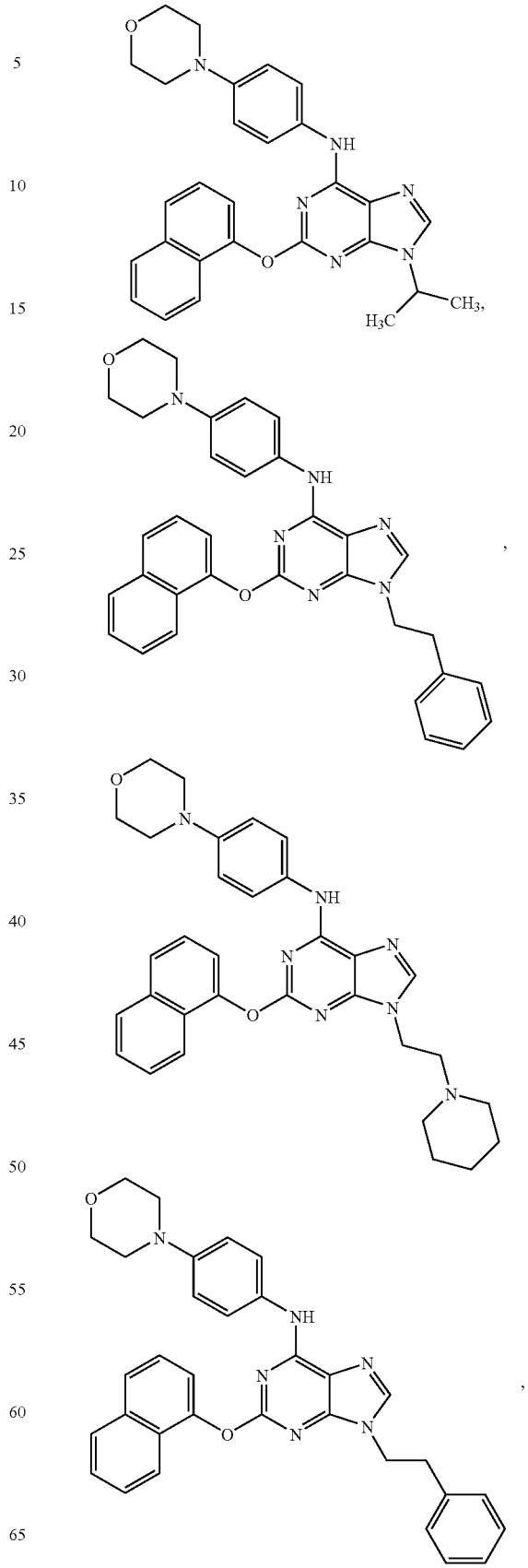

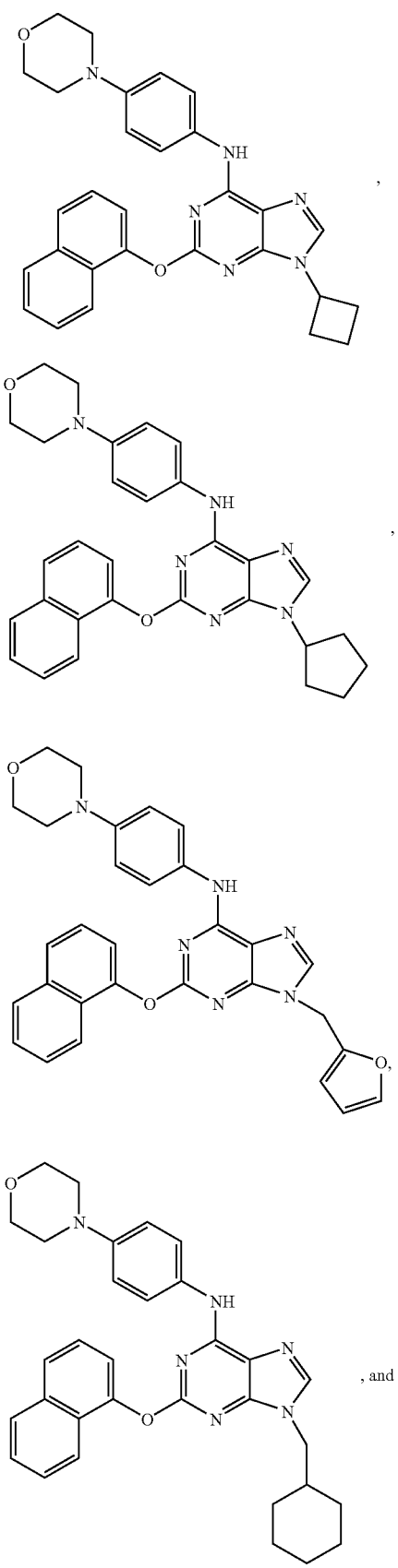

10. A compound of claim 1, wherein the compound is:

11. A pharmaceutical composition comprising a compound of claim 1 and a pharmaceutically acceptable carrier.

12. A method of inducing osteogenesis, the method comprising:
contacting a mammalian cell with a compound of claim 1, whereby the mammalian cell differentiates into a cell of an osteoblast lineage.

13. The method of claim 12, wherein said compound of claim 1 is in a pharmaceutically acceptable carrier.

14. The method of claim 12, wherein the mammalian cell is in a mammal.

15. The method of claim 14, wherein the step of contacting is by oral administration of the compound to the mammal.

16. The method of claim 14, wherein the step of contacting is by intravenous administration of the compound to the mammal.

17. The method of claim 14, wherein the step of contacting is by subcutaneous administration of the compound to the mammal.

18. The method of claim 14, wherein the step of contacting is by intraperitoneal administration of the compound to the mammal.

19. The method of claim 12, further comprising detecting differentiation of the mammalian cell into a cell of an osteoblast lineage.

20. The method of claim 19, whereby differentiation of the mammalian cell into a cell of an osteoblast lineage is detected by detecting expression of an osteogenesis marker gene.

21. The method of claim 20, wherein the osteogenesis marker gene is a gene selected from the group consisting of alkaline phosphatase, collagen type I, osteocalcin, and osteoponin.

22. The method of claim 19, whereby differentiation of the mammalian cell into a cell of an osteoblast lineage is detected by detecting expression of a bone specific transcription factor.

23. The method of claim 22, wherein the bone specific transcription factor is Cbfa1/Runx2.

24. The method of claim 12, wherein the mammalian cell is a stem cell.

25. The method of claim 24, wherein the stem cell is a mesenchymal stem cell.

26. The method of claim 25, wherein the mesenchymal stem cell is isolated from a mouse.

27. The method of claim 26, wherein the mesenchymal stem cell is murine embryonic mesoderm fibroblast cell.

28. The method of claim 25, wherein the mesenchymal stem cell is isolated from a primate.

29. The method of claim 28, wherein the primate is a human.

30. The method of claim 12, wherein the mammalian cell is further contacted with bone morphogenetic protein 4 (BMP-4).

31. The method of claim 30, wherein the mammalian cell is a pre-adipocyte cell.

32. The method of claim 30, wherein the mammalian cell is a myoblast cell.

33. The method of claim 12, wherein the mammalian cell is attached to a solid support.

34. The method of claim 33, wherein the solid support is a three dimensional matrix.

35. The method of claim 33, wherein the solid support is a planar surface.

36. A method of inducing osteogenesis, the method comprising:
    contacting a mammalian cell with a compound of claim 10, whereby the mammalian cell differentiates into a cell of an osteoblast lineage.

37. The method of claim 36, wherein the mammalian cell is in a mammal.

38. The method of claim 36, wherein the step of contacting is by oral administration of the compound to the mammal.

39. The method of claim 36, wherein the step of contacting is by intravenous administration of the compound to the mammal.

40. The method of claim 36, wherein the step of contacting is by subcutaneous administration of the compound to the mammal.

41. The method of claim 36, wherein the step of contacting is by intraperitoneal administration of the compound to the mammal.

42. A method of treating a bone disorder, the method comprising:
    contacting a mammalian cell with a compound of claim 1, whereby the mammalian cell differentiates into a cell of an osteoblast lineage, wherein the bone disorder is associated with defective osteoblasts.

43. The method of claim 42 wherein the bone disorder is osteoporosis.

44. The method of claim 42, further comprising administering the cell of an osteoblast lineage to an individual with the disorder, thereby treating the disorder.

45. The method of claim 44, wherein the administration is by surgical implantation.

46. A pharmaceutical composition comprising a compound of claim 8 and a pharmaceutically acceptable carrier.

47. A pharmaceutical composition comprising a compound of claim 9 and a pharmaceutically acceptable carrier.

48. A method of inducing osteogenesis, the method comprising:
    contacting a mammalian cell with a compound of claim 8, whereby the mammalian cell differentiates into a cell of an osteoblast lineage.

49. A method of inducing osteogenesis, the method comprising:
    contacting a mammalian cell with a compound of claim 9, whereby the mammalian cell differentiates into a cell of an osteoblast lineage.

50. A method of treating a bone disorder, the method comprising:
    contacting a mammalian cell with a compound of claim 8, whereby the mammalian cell differentiates into a cell of an osteoblast lineage, wherein the bone disorder is associated with defective osteoblasts.

51. A method of treating a bone disorder, the method comprising:
    contacting a mammalian cell with a compound of claim 9, whereby the mammalian cell differentiates into a cell of an osteoblast lineage, wherein the bone disorder is associated with defective osteoblasts.

* * * * *